(12) United States Patent
Bodepudi et al.

(10) Patent No.: US 9,410,195 B2
(45) Date of Patent: Aug. 9, 2016

(54) METHODS AND REAGENTS FOR REDUCING NON-SPECIFIC AMPLIFICATION

(71) Applicant: Roche Molecular Systems, Inc., Pleasanton, CA (US)

(72) Inventors: Veeraiah Bodepudi, San Ramon, CA (US); Nancy Schoenbrunner, Charlestown, MA (US); Stephen Will, Oakland, CA (US)

(73) Assignee: ROCHE MOLECULAR SYSTEMS, INC., Pleasanton, CA (US)

( * ) Notice: Subject to any disclaimer, the term of this patent is extended or adjusted under 35 U.S.C. 154(b) by 0 days.

(21) Appl. No.: 14/802,481

(22) Filed: Jul. 17, 2015

(65) Prior Publication Data

US 2015/0322502 A1 Nov. 12, 2015

Related U.S. Application Data

(62) Division of application No. 13/710,824, filed on Dec. 11, 2012, now Pat. No. 9,115,394.

(60) Provisional application No. 61/579,317, filed on Dec. 22, 2011.

(51) Int. Cl.
*C07H 21/04* (2006.01)
*C12Q 1/68* (2006.01)

(52) U.S. Cl.
CPC ............. *C12Q 1/686* (2013.01); *C07H 21/04* (2013.01); *C12Q 1/6848* (2013.01)

(58) Field of Classification Search
None
See application file for complete search history.

(56) References Cited

U.S. PATENT DOCUMENTS

| | | | |
|---|---|---|---|
| 5,525,494 A * | 6/1996 | Newton | C07H 21/00 435/91.2 |
| 6,001,611 A | 12/1999 | Will | |
| 6,200,757 B1 | 3/2001 | Kurn et al. | |
| 6,509,157 B1 | 1/2003 | Martinez | |
| 6,548,251 B1 | 4/2003 | Kozyavkin et al. | |
| 6,794,142 B2 | 9/2004 | Laird et al. | |
| 7,205,129 B1 | 4/2007 | Dean et al. | |
| 7,211,382 B2 | 5/2007 | Zhao et al. | |
| 7,851,148 B2 | 12/2010 | Han | |
| 2009/0148891 A1 | 6/2009 | Bauer et al. | |
| 2012/0064511 A1 | 3/2012 | Leying et al. | |
| 2012/0190008 A1 | 7/2012 | Eickhoff et al. | |

FOREIGN PATENT DOCUMENTS

WO 0175139 A1 10/2001
WO PCT/EP2012/005230 4/2013

OTHER PUBLICATIONS

Stricker et al. Development of a Scorpion probe-based real-time PCR for the sensitive quantification of *Bacteroides* sp. ribosomal DNA from human and cattle origin and evaluation in spring water matrices. Microbiol. Res. (2008) vol. 163, No. 2, pp. 140-147.*

Afonina, Irina, et al., 1996, "Sequence-specific arrest of primer extension on single-stranded DNA by an oligonucleotide-minor groove binder conjugate", Proceedings of the National Academy of Sciences, 93:3199-3204.

Afonina, I. A., et al., 2002, "Minor Groove Binder-Conjugated DNA Probes for Quantitative DNA Detection by Hybridization-Triggered Fluorescence", BioTechniques, 32(4):940-949.

Choi, Jeong-Yun, et al., 2004, "Analysis of the Effect of Bulk at N2-Alkylguanine DNA on Catalytic Efficiency and Fidelity of the Processive DNA Polymerases Bacteriophage T7 Exonuclease- and HIV-1 Reverse Transcriptase", The Journal of Biological Chemistry, 279(18):19217-19229.

Choi, Jeong-Yun, et al., 2006, "Translesion Synthesis across Bulky N2-Alkyl Guanine DNA Adducts by Human DNA Polymerase K", Journal of Biological Chemistry, 281(30):21062-21065.

Kutyavin, I.V. et al, 2000, "3'-minor groove binder-DNA probes increase sequence specificity at PCR extension temperatures", Nucleic Acids Research, 28 (2):655-661.

* cited by examiner

*Primary Examiner* — David Thomas
(74) *Attorney, Agent, or Firm* — David J. Chang

(57) ABSTRACT

The present invention provides reagents for use in the amplification of nucleic acids. Amplification carried out using oligonucleotides containing modified nucleotides can result in less non-specific amplification compared to amplification carried out using unmodified oligonucleotides.

3 Claims, 14 Drawing Sheets

(A)

N²-Benzyl Deoxyguanosine (B)

Base pair between N²-Benzyl Deoxyguanosine and Deoxycytidine

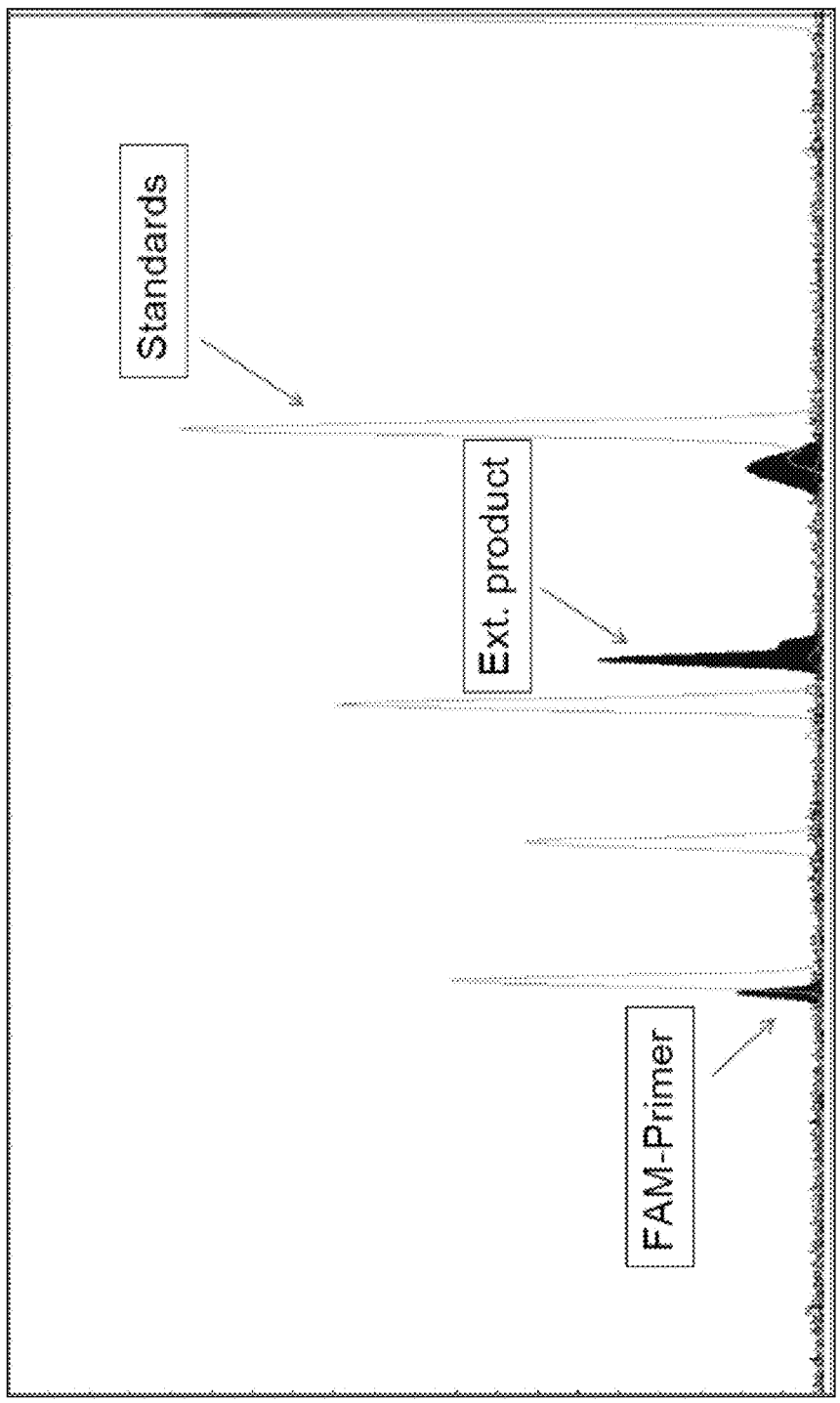

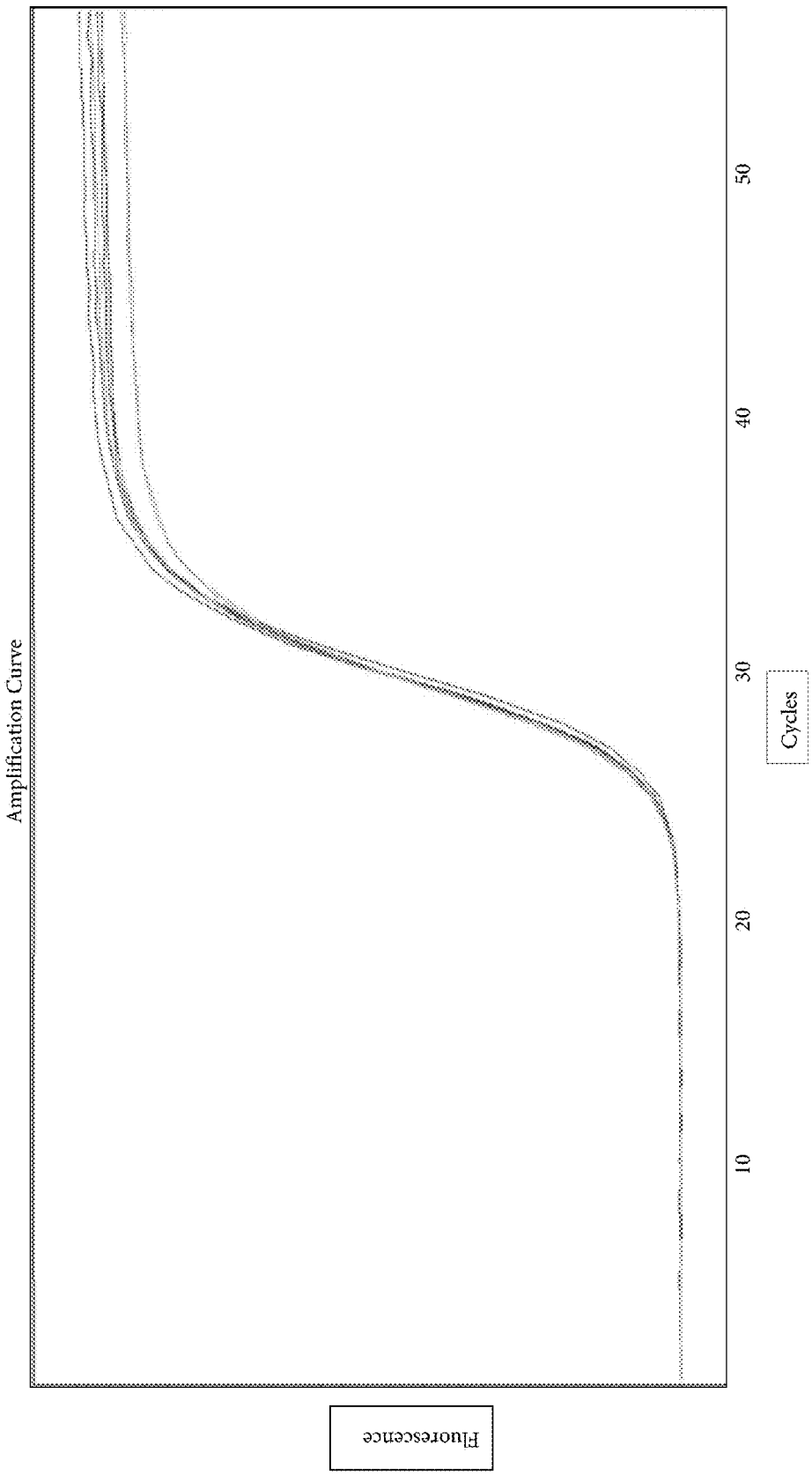

METHODS AND REAGENTS FOR REDUCING NON-SPECIFIC AMPLIFICATION

CROSS REFERENCE TO RELATED INVENTION

This application is a divisional of U.S. application Ser. No. 13/710,824 filed on Dec. 11, 2012, which claims the benefit of U.S. Provisional Patent Application Ser. No. 61/579,317, filed on Dec. 22, 2011, the contents of each are incorporated by reference herein in their entirety.

REFERENCE TO SEQUENCE LISTING

This application contains a Sequence Listing submitted as an electronic text file named "26108_US1_Sequence_Listing.txt", having a size in bytes of 15 kb, and created on Dec. 10, 2012. The information contained in this electronic file is hereby incorporated by reference in its entirety pursuant to 37 CFR §1.52(e)(5).

FIELD OF THE INVENTION

The present invention relates to the field of molecular biology and nucleic acid chemistry. More specifically it relates to methods and reagents for improving the reliability of nucleic acid amplification reactions.

BACKGROUND OF THE INVENTION

The invention of the polymerase chain reaction (PCR) made possible the in vitro amplification of nucleic acid sequences. PCR is described in U.S. Pat. Nos. 4,683,195; 4,683,202; and 4,965,188; Saiki et al., 1985, Science 230: 1350-1354; Mullis et al., 1986, Cold Springs Harbor Symp. Quant. Biol. 51:263-273; and Mullis and Faloona, 1987, Methods Enzymol. 155:335-350; each of which is incorporated herein by reference. The development and application of PCR are described extensively in the literature. For example, a range of PCR-related topics are discussed in PCR Technology—principles and applications for DNA amplification, 1989, (ed. H. A. Erlich) Stockton Press, New York; PCR Protocols: A guide to methods and applications, 1990, (ed. M. A. Innis et al.) Academic Press, San Diego; and PCR Strategies, 1995, (ed. M. A. Innis et al.) Academic Press, San Diego; each of which is incorporated herein by reference. Commercial vendors, such as Applied Biosystems (Foster City, Calif.), market PCR reagents and publish PCR protocols.

Since the original publication of nucleic acid amplification, various primer-based nucleic acid amplification methods have been described including, but not limited to, the strand displacement assay (Walker et al., 1992, Proc. Natl. Acad. Sci. USA 89:392-396, Walker et al. 1992, Nucleic Acids Res. 20:1691-1696, and U.S. Pat. No. 5,455,166) and the transcription-based amplification systems, including the methods described in U.S. Pat. Nos. 5,437,990; 5,409,818; and 5,399,491; the transcription amplification system (TAS) (Kwoh et al., 1989, Proc. Natl. Acad. Sci. USA 86:1173-1177); and self-sustained sequence replication (3SR) (Guatelli et al., 1990, Proc. Natl. Acad. Sci. USA 87:1874-1878 and WO 92/08800). All of the above references are incorporated herein by reference. A survey of amplification systems is provided in Abramson and Myers, 1993, Current Opinion in Biotechnology 4:41-47, incorporated herein by reference.

Specificity of primer-based amplification reactions largely depends on the specificity of primer hybridization and extension. Under the elevated temperatures used in a typical amplification, the primers hybridize only to the intended target sequence. However, amplification reaction mixtures are typically assembled at room temperature, well below the temperature needed to insure primer hybridization specificity. Under such less stringent conditions, the primers may bind non-specifically to other only partially complementary nucleic acid sequences or to other primers and initiate the synthesis of undesired extension products, which can be amplified along with the target sequence. Amplification of non-specific primer extension products can compete with amplification of the desired target sequences and can significantly decrease the efficiency of the amplification of the desired sequence.

One frequently observed type of non-specific amplification product is a template-independent artifact of amplification reactions referred to as "primer dimer". Primer dimer is a double-stranded fragment whose length typically is close to the sum of the two primer lengths and appears to occur when one primer is extended over the other primer. The resulting extension product forms an undesired template which, because of its short length, is amplified efficiently.

Non-specific amplification can be reduced by reducing the formation of primer extension products prior to the start of the reaction. In one method, referred to as a "hot-start" protocol, one or more critical reagents are withheld from the reaction mixture until the temperature is raised sufficiently to provide the necessary hybridization specificity. Manual hot-start methods, in which the reaction tubes are opened after the initial high temperature incubation step and the missing reagents are added, are labor intensive and increase the risk of contamination of the reaction mixture. Alternatively, a heat sensitive material, such as wax, can be used to separate or sequester reaction components, as described in U.S. Pat. No. 5,411,876, incorporated herein by reference, and Chou et al., 1992, Nucl. Acids Res. 20(7):1717-1723, incorporated herein by reference. In these methods, a high temperature pre-reaction incubation melts the heat sensitive material, thereby allowing the reagents to mix.

Another method of reducing the formation of primer extension products prior to the start of the reaction relies on the heat-reversible inactivation of the DNA polymerase. U.S. Pat. Nos. 5,773,258 and 5,677,152, both incorporated herein by reference, describe DNA polymerases reversibly modified by the covalent attachment of a modifier group. Incubation of the inactivated DNA polymerase at high temperature results in cleavage of the modifier-enzyme bond, thereby reactivating the enzyme.

Non-covalent reversible inhibition of a DNA polymerase by DNA polymerase-specific antibodies is described in U.S. Pat. No. 5,338,671, incorporated herein by reference.

Non-specific amplification also can be reduced by enzymatically degrading extension products formed prior to the start of the reaction using the methods described in U.S. Pat. No. 5,418,149, which is incorporated herein by reference. The degradation of newly-synthesized extension products is achieved by incorporating into the reaction mixture dUTP and UNG, and incubating the reaction mixture at 45-60° C. prior to carrying out the amplification reaction. Primer extension results in the formation of uracil-containing DNA, which is degraded by UNG under the pre-amplification conditions. A disadvantage of this method is that the degradation of extension product competes with the formation of extension product and the elimination of non-specific primer extension product may be less complete. An advantage of this method is that uracil-containing DNA introduced into the reaction mixture as a contamination from a previous reaction is also degraded and, thus, the method also reduces the problem of contamination of a PCR by the amplified nucleic acid from previous reactions.

Another method of reducing the formation of primer extension products prior to the start of the reaction relies on the use of primers modified at or near the 3' end by the addition of a moiety to an exocyclic amine, as described in U.S. Pat. No. 6,001,611, incorporated herein by reference.

Conventional techniques of molecular biology and nucleic acid chemistry, which are within the skill of the art, are fully explained fully in the literature. See, for example, Sambrook et al., 1989, Molecular Cloning—A Laboratory Manual, Cold Spring Harbor Laboratory, Cold Spring Harbor, N.Y.; Oligonucleotide Synthesis (M. J. Gait, ed., 1984); Nucleic Acid Hybridization (B. D. Hames and S. J. Higgins. eds., 1984); PCR Technology—principles and applications for DNA amplification, 1989, (ed. H. A. Erlich) Stockton Press, New York; PCR Protocols: A guide to methods and applications, 1990, (ed. M. A. Innis et al.) Academic Press, San Diego; and PCR Strategies, 1995, (ed. M. A. Innis et al.) Academic Press, San Diego; all of which are incorporated herein by reference.

SUMMARY OF THE INVENTION

The present invention is based on the surprising discovery that in certain amplification reactions, particularly in reactions that contain multiple primers and probes for the amplification and detection of multiple target nucleic acids (e.g. multiplex PCR reactions), probe(s) can serve as a temple which could lead to non-specific amplification which in turn would give the signal for false-positives. To reduce probe based non-specific amplification in PCR, minor groove modifiers which interferes with the activity of DNA polymerase but which is still capable of base pairing with a complementary nucleotide can be used. One such example of a minor groove modifier is the deoxyguanosine analog, $N^2$-benzyl guanosine ($N^2$-benzyl-dG), which is the subject of the present invention as described herein.

Thus one aspect of the present invention relates to a method of preventing the extension by DNA polymerase of a primer oligonucleotide that hybridizes to a template nucleotide sequence in an assay employing the extension of a primer in a template-dependent manner comprising, incorporating a minor groove binder on the template nucleotide sequence wherein the primer oligonucleotide is incapable of being extended by more than 2 nucleotides beyond the position of the minor groove binder. In one embodiment, the minor groove binder is a modified nucleoside. In another embodiment, the modified nucleoside is $N^2$-benzyl-deoxyguanosine ($N^2$-benzyl-dG).

Another aspect of the present invention relates to a method of reducing or preventing non-specific amplification of nucleic acid during an amplification reaction comprising providing at least one pair of primer oligonucleotides capable of amplifying a target nucleic acid sequence; providing a probe oligonucleotide that incorporates a minor groove binder that blocks the extension of the primer oligonucleotide by a DNA polymerase by more than 2 nucleotides beyond the position of the minor groove binder when the primer oligonucleotide hybridizes to the probe oligonucleotide. In one embodiment, the minor groove binder is a modified nucleoside. In another embodiment, the modified nucleoside is $N^2$-benzyl-deoxyguanosine ($N^2$-benzyl-dG).

A third aspect of the present invention relates to a reaction mixture for the amplification of nucleic acids, comprising at least one pair of primer oligonucleotides and at least one probe oligonucleotide that incorporates a $N^2$-benzyl-dG nucleotide.

A fourth aspect of the present invention relates to a kit for the amplification of nucleic acids, comprising at least one pair of primer oligonucleotides, at least one probe oligonucleotide that incorporates a $N^2$-benzyl-dG nucleotide, at least one nucleotide-incorporating biocatalyst, nucleoside triphosphates, a buffer suitable for the amplification of nucleic acids by the at least one nucleotide-incorporating biocatalyst, and a set of instructions for performing the amplification of nucleic acids.

DETAILED DESCRIPTION OF THE INVENTION

Definitions

Figure 1:
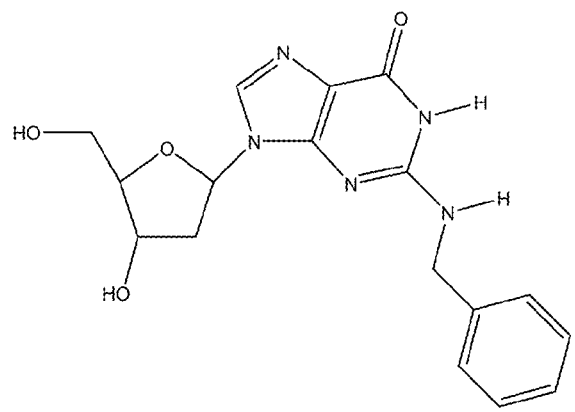
FIG. 1 shows (A) the structure of $N^2$-benzyl-dG and (B) base pairing between $N^2$-benzyl-dG and deoxycytosine (dC).
Figure 1:
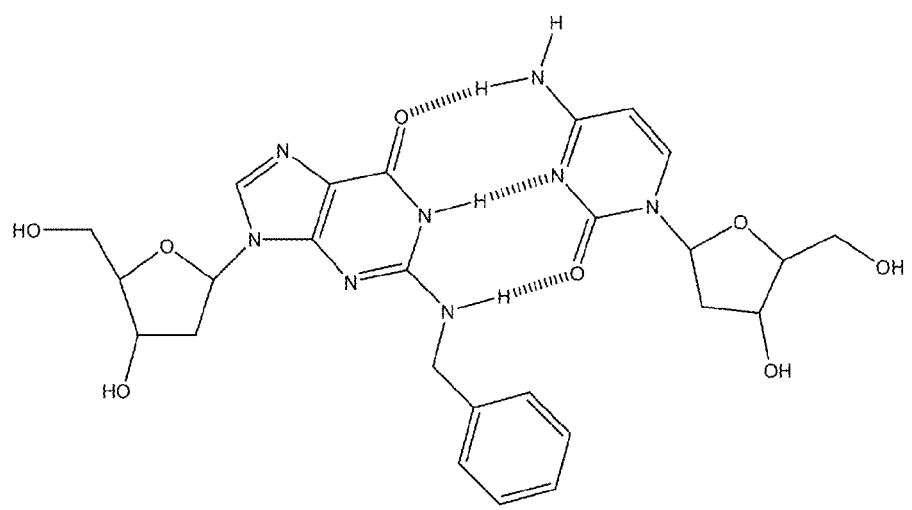

Unless defined otherwise, all technical and scientific terms used herein have the same meaning as commonly understood by one of ordinary skill in the art to which this invention pertains. In describing and claiming the present invention, the following definitions will be used.

The term "nucleic acid" refers to polymers of nucleotides (e.g., ribonucleotides, deoxyribonucleotides, nucleotide analogs etc.) and comprising deoxyribonucleic acids (DNA), ribonucleic acids (RNA), DNA-RNA hybrids, oligonucleotides, polynucleotides, aptamers, peptide nucleic acids (PNAs), PNA-DNA conjugates, PNA-RNA conjugates, etc., that comprise nucleotides covalently linked together, either in a linear or branched fashion. A nucleic acid is typically single-stranded or double-stranded and will generally contain phosphodiester bonds, although in some cases, nucleic acid analogs are included that may have alternate backbones, including, for example, phosphoramide (Beaucage et al. (1993) Tetrahedron 49(10):1925); phosphorothioate (Mag et al. (1991) Nucleic Acids Res. 19:1437; and U.S. Pat. No. 5,644,048), phosphorodithioate (Briu et al. (1989) J. Am. Chem. Soc. 111:2321), O-methylphophoroamidite linkages (see Eckstein, Oligonucleotides and Analogues: A Practical Approach, Oxford University Press (1992)), and peptide nucleic acid backbones and linkages (see, Egholm (1992) J. Am. Chem. Soc. 114:1895). Other analog nucleic acids include those with positively charged backbones (Denpcy et al. (1995) Proc. Natl. Acad. Sci. USA 92: 6097); non-ionic backbones (U.S. Pat. Nos. 5,386,023, 5,637,684, 5,602,240, 5,216,141 and 4,469,863) and non-ribose backbones, including those described in U.S. Pat. Nos. 5,235,033 and 5,034,506. Nucleic acids containing one or more carbocyclic sugars are also included within the definition of nucleic acids (see Jenkins et al. (1995) Chem. Soc. Rev. pp. 169-176), and analogs are also described in, e.g., Rawls, C & E News Jun. 2, 1997 page 35. These modifications of the ribose-phosphate backbone may be done to facilitate the addition of additional moieties such as labels, or to alter the stability and half-life of such molecules in physiological environments.

In addition to the naturally occurring heterocyclic bases that are typically found in nucleic acids (e.g., adenine, guanine, thymine, cytosine, and uracil), nucleotide analogs also may include non-naturally occurring heterocyclic bases, such as those described in, e.g., Seela et al. (1999) Helv. Chim. Acta 82:1640. Certain bases used in nucleotide analogs act as melting temperature (Tm) modifiers. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, which is incorporated herein by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytidine; 5-fluorocytidine; 5-chlorocytidine; 5-iodocytidine; 5-bromocytidine; 5-methylcytidine; 5-propynylcytidine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

A "nucleoside" refers to a nucleic acid component that comprises a base or basic group (comprising at least one homocyclic ring, at least one heterocyclic ring, at least one aryl group, and/or the like) covalently linked to a sugar moiety (a ribose sugar or a deoxyribose sugar), a derivative of a sugar moiety, or a functional equivalent of a sugar moiety (e.g. a carbocyclic ring). For example, when a nucleoside includes a sugar moiety, the base is typically linked to a 1'-position of that sugar moiety. As described above, a base can be a naturally occurring base or a non-naturally occurring base. Exemplary nucleosides include ribonucleosides, deoxyribonucleosides, dideoxyribonucleosides and carbocyclic nucleosides.

A "nucleotide" refers to an ester of a nucleoside, e.g., a phosphate ester of a nucleoside, having one, two, three or more phosphate groups covalently linked to a 5' position of a sugar moiety of the nucleoside.

A "purine nucleotide" refers to a nucleotide that comprises a purine base, whereas a "pyrimidine nucleotide" refers to a nucleotide that comprises a pyrimidine base.

A "modified nucleotide" refers to rare or minor nucleic acid bases, nucleotides and modifications, derivations, or analogs of conventional bases or nucleotides and includes synthetic nucleotides having modified base moieties and/or modified sugar moieties (see, Protocols for Oligonucleotide Conjugates, Methods in Molecular Biology, Vol. 26 (Suhier Agrawal, Ed., Humana Press, Totowa, N.J., (1994)); and Oligonucleotides and Analogues, A Practical Approach (Fritz Eckstein, Ed., IRL Press, Oxford University Press, Oxford); both incorporated herein by reference.

An "oligonucleotide" refers to a nucleic acid polymer that includes at least two, but typically 5-50 nucleotides and more typically, between 15 and 35 nucleotides. The exact size of an oligonucleotide generally depends on various factors, including the ultimate function or use of the oligonucleotide. Oligonucleotides may be prepared by any suitable method known in the art, including, for example, cloning and restriction digestion of appropriate sequences, or direct chemical synthesis by a method such as the phosphotriester method of Narang et al. (1979) Meth. Enzymol. 68:90-99; the phosphodiester method of Brown et al. (1979) Meth. Enzymol. 68:109-151; the diethylphosphoramidite method of Beaucage et al. (1981) Tetrahedron Lett. 22:1859-1862; the triester method of Matteucci et al. (1981) J. Am. Chem. Soc. 103: 3185-3191; automated synthesis methods; the solid support method of U.S. Pat. No. 4,458,066 or any other chemical method known in the art.

A "Watson-Crick base pairing" or simply "base pairing" refers to "conventional" hydrogen bonding within a double-stranded nucleic acid molecule. Watson-Crick base pairing is hydrogen bonding between adenine and thymine, between guanine and cytosine, between adenine and uracil, and between analogs of these bases.

As used herein, the terms "hybridization" and "annealing" and the like are used interchangeably and refer to the base-pairing interaction of one polynucleotide with another polynucleotide (typically an antiparallel polynucleotide) that results in formation of a duplex or other higher-ordered structure, typically termed a hybridization complex. The primary interaction between the antiparallel polynucleotide molecules is typically base specific, e.g., A/T and G/C, by Watson/Crick and/or Hoogsteen-type hydrogen bonding. It is not a requirement that two polynucleotides have 100% complementarity over their full length to achieve hybridization. In some aspects, a hybridization complex can form from intermolecular interactions, or alternatively, can form from intramolecular interactions.

As used herein, the terms "amplification," "amplifying" and the like refer generally to any process that results in an increase in the copy number of a molecule or set of related molecules. As it applies to polynucleotide molecules, amplification means the production of multiple copies of a polynucleotide molecule, or a portion of a polynucleotide molecule, typically starting from a small amount of a polynucleotide (e.g., a viral genome), where the amplified material (e.g., a viral PCR amplicon) is typically detectable. Amplification of polynucleotides encompasses a variety of chemical and enzymatic processes. The generation of multiple DNA copies from one or a few copies of a template DNA molecule during a polymerase chain reaction (PCR), a strand displacement amplification (SDA) reaction, a transcription mediated amplification (TMA) reaction, a nucleic acid sequence-based amplification (NASBA) reaction, or a ligase chain reaction (LCR) are forms of amplification. Amplification is not limited to the strict duplication of the starting molecule. For example, the generation of multiple cDNA molecules from a limited amount of viral RNA in a sample using RT-PCR is a form of amplification. Furthermore, the generation of multiple RNA molecules from a single DNA molecule during the process of transcription is also a form of amplification.

In some embodiments, amplification is optionally followed by additional steps, for example, but not limited to, labeling, sequencing, purification, isolation, hybridization, size resolution, expression, detecting and/or cloning.

As used herein, the term "polymerase chain reaction" (PCR) refers to a method for amplification well known in the art for increasing the concentration of a segment of a target polynucleotide in a sample, where the sample can be a single polynucleotide species, or multiple polynucleotides. Generally, the PCR process consists of introducing a molar excess of two or more extendable oligonucleotide primers to a reaction mixture comprising the desired target sequence(s), where the primers are complementary to opposite strands of the double stranded target sequence. The reaction mixture is subjected to a program of thermal cycling in the presence of a DNA polymerase, resulting in the amplification of the desired target sequence flanked by the DNA primers. Reverse transcriptase PCR (RT-PCR) is a PCR reaction that uses RNA template and a reverse transcriptase, or an enzyme having reverse transcriptase activity, to first generate a single stranded DNA molecule prior to the multiple cycles of DNA-dependent DNA polymerase primer elongation. Multiplex PCR refers to PCR reactions that produce more than one amplified product in a single reaction, typically by the inclusion of more than two primers in a single reaction. Methods for a wide variety of PCR applications are widely known in the art, and described in many sources, for example, Ausubel et al. (eds.), Current Protocols in Molecular Biology, Section 15, John Wiley & Sons, Inc., New York (1994).

A "primer nucleic acid" or "primer" is an oligonucleotide that can hybridize to a template nucleic acid and permit chain extension or elongation using a nucleotide incorporating biocatalyst. Although other primer lengths are sometimes utilized, primers typically range from 15 to 35 nucleotides. Short primer nucleic acids generally utilize cooler temperatures to form sufficiently stable hybrid complexes with template nucleic acids. A primer nucleic acid that is at least partially complementary to a subsequence of a template nucleic acid is typically sufficient to hybridize with the template nucleic acid for extension to occur. However, the success of the extension generally requires greater complementarity (i.e. fewer mismatches with the template) at the 3'-end of the primer. A primer nucleic acid can be labeled, if desired, by incorporating a label detectable by radiological, spectroscopic, photochemical, biochemical, immunochemical, or chemical techniques.

An "extended primer" refers to a primer to which one or more additional nucleotides have been added. "Primer extension" is the action of the enzyme by which additional nucleotides are added to the primer.

A "template nucleic acid", "template" or "target" refers to a nucleic acid to which a primer nucleic acid can hybridize and be extended under suitable conditions. In the context of nucleic acid amplification, "target" is preferably a region of double stranded nucleic acid, consisting of the sequences at least partially complementary to at least two primer sequences and the intervening sequence. A target can also be a single stranded nucleic acid, consisting of a sequence at least partially complementary to one primer and a sequence partially identical to the second primer. Template nucleic acids can exist as isolated nucleic acid fragments or be a part of a larger nucleic acid fragment. Target nucleic acids can be derived or isolated from essentially any source, such as cultured microorganisms, uncultured microorganisms, complex biological mixtures, tissues, sera, ancient or preserved tissues or samples, environmental isolates or the like. Further, template nucleic acids optionally include or are derived from cDNA, RNA, genomic DNA, cloned genomic DNA, genomic DNA libraries, enzymatically fragmented DNA or RNA, chemically fragmented DNA or RNA, physically fragmented DNA or RNA, or the like. Template nucleic acids can also be chemically synthesized using techniques known in the art.

As used herein, the term "probe" refers typically to a polynucleotide that is capable of hybridizing to a target nucleic acid of interest. Typically, but not exclusively, a probe is associated with a suitable label or reporter moiety so that the probe (and therefore its target) can be detected, visualized, measured and/or quantitated. Detection systems for labelled probes include, but are not limited to, the detection of fluorescence, fluorescence quenching (e.g., when using a FRET pair detection system), enzymatic activity, absorbance, molecular mass, radioactivity, luminescence or binding properties that permit specific binding of the reporter (e.g., where the reporter is an antibody). In some embodiments, a probe can be an antibody, rather than a polynucleotide, that has binding specificity for a nucleic acid nucleotide sequence of interest. It is not intended that the present invention be limited to any particular probe label or probe detection system. The source of the polynucleotide used in the probe is not limited, and can be produced synthetically in a non-enzymatic system, or can be a polynucleotide (or a portion of a polynucleotide) that is produced using a biological (e.g., enzymatic) system (e.g., in a bacterial cell).

Typically, a probe is sufficiently complementary to a specific target sequence contained in a nucleic acid to form a stable hybridization complex with the target sequence under a selected hybridization condition, such as, but not limited to, a stringent hybridization condition. A hybridization assay carried out using the probe under sufficiently stringent hybridization conditions permits the selective detection of a specific target sequence.

As used herein, a primer is "specific" for a template sequence if the number of mismatches present between the primer sequence and the target sequence is less than the number of mismatches present between the primer sequence and non-target sequences which may be present in the sample. Hybridization conditions can be chosen under which stable duplexes are formed only if the number of mismatches present is no more than the number of mismatches present between the primer sequence and the target sequence. Under such conditions, the primer can form a stable duplex only with a target sequence. Thus, the use of target-specific primers under suitably stringent amplification of those target sequences which contain the target primer binding sites. The use of sequence-specific amplification conditions enables the specific amplification of those target sequences which contain the exactly complementary primer binding sites.

The term "non-specific amplification" refers to the amplification of nucleic acid sequences other than the target sequence which results from primers hybridizing to sequences other than the target sequence and then serving as a substrate for primer extension. The hybridization of a primer to a non-target sequence is referred to as "non-specific hybridization" and can occur during the lower temperature, reduced stringency, pre-amplification conditions.

As used herein, the term "amplicon" refers to a polynucleotide molecule (or collectively the plurality of molecules) produced following the amplification of a particular target nucleic acid. The amplification method used to generate the amplicon can be any suitable method, most typically, for example, by using a PCR methodology. An amplicon is typically, but not exclusively, a DNA amplicon. An amplicon can be single-stranded or double-stranded, or in a mixture thereof in any concentration ratio.

As used herein, the expression "real-time detection of amplicon accumulation" refers to the detection of, and typically the quantitation thereof, of a specific amplicon or amplicons, as the amplicon(s) is/are being produced (typically by PCR) without the need for a detection or quantitation step following the completion of the amplification. The terms "real-time PCR" or "kinetic PCR" refer to real-time detection and/or quantitation of amplicon generated in a PCR.

A common method for real-time detection of amplicon accumulation is by a 5'-nuclease assay, also termed a fluorogenic 5'-nuclease assay, e.g., a TaqMan analysis; see, Holland et al., Proc. Natl. Acad. Sci. USA 88:7276-7280 (1991); and Heid et al., Genome Research 6:986-994 (1996). In the TaqMan PCR procedure, two oligonucleotide primers are used to generate an amplicon specific to the PCR reaction. A third oligonucleotide (the TaqMan probe) is designed to hybridize with a nucleotide sequence in the amplicon located between the two PCR primers. The probe may have a structure that is non-extendible by the DNA polymerase used in the PCR reaction, and is typically (but not necessarily) colabeled with a fluorescent reporter dye and a quencher moiety in close proximity to one another. The emission from the reporter dye is quenched by the quenching moiety when the fluor and quencher are in close proximity, as they are on the probe. In some cases, the probe may be labeled with only a fluorescent reporter dye or another detectable moiety.

The TaqMan PCR reaction uses a thermostable DNA-dependent DNA polymerase that possesses a 5'-3' nuclease activity. During the PCR amplification reaction, the 5'-3' nuclease activity of the DNA polymerase cleaves the labeled probe that is hybridized to the amplicon in a template-dependent manner. The resultant probe fragments dissociate from the primer/template complex, and the reporter dye is then free from the quenching effect of the quencher moiety. Approximately one molecule of reporter dye is liberated for each new amplicon molecule synthesized, and detection of the unquenched reporter dye provides the basis for quantitative interpretation of the data, such that the amount of released fluorescent reporter dye is directly proportional to the amount of amplicon template.

One measure of the TaqMan assay data is typically expressed as the threshold cycle (CT). Fluorescence levels are recorded during each PCR cycle and are proportional to the amount of product amplified to that point in the amplification reaction. The PCR cycle when the fluorescence signal is first recorded as statistically significant, or where the fluorescence signal is above some other arbitrary level (e.g., the arbitrary fluorescence level, or AFL), is the threshold cycle (CT).

Protocols and reagents for 5'-nuclease assays are well known to one of skill in the art, and are described in various sources. For example, 5'-nuclease reactions and probes are described in U.S. Pat. No. 6,214,979, entitled "HOMOGENEOUS ASSAY SYSTEM," issued Apr. 10, 2001 to Gelfand et al.; U.S. Pat. No. 5,804,375, entitled "REACTION MIXTURES FOR DETECTION OF TARGET NUCLEIC ACIDS," issued Sep. 8, 1998 to Gelfand et al.; U.S. Pat. No. 5,487,972, entitled "NUCLEIC ACID DETECTION BY THE 5'-3' EXONUCLEASE ACTIVITY OF POLYMERASES ACTING ON ADJACENTLY HYBRIDIZED OLIGONUCLEOTIDES," issued Jan. 30, 1996 to Gelfand et al.; and U.S. Pat. No. 5,210,015, entitled "HOMOGENEOUS ASSAY SYSTEM USING THE NUCLEASE ACTIVITY OF A NUCLEIC ACID POLYMERASE," issued May 11, 1993 to Gelfand et al., all of which are incorporated by reference.

Variations in methodologies for real-time amplicon detection are also known, and in particular, where the 5'-nuclease probe is replaced by double-stranded DNA intercalating dye resulting in fluorescence that is dependent on the amount of double-stranded amplicon that is present in the amplification reaction. See, for example, U.S. Pat. No. 6,171,785, entitled "METHODS AND DEVICES FOR HOMOGENEOUS NUCLEIC ACID AMPLIFICATION AND DETECTOR," issued Jan. 9, 2001 to Higuchi; and U.S. Pat. No. 5,994,056, entitled "HOMOGENEOUS METHODS FOR NUCLEIC ACID AMPLIFICATION AND DETECTION," issued Nov. 30, 1999 to Higuchi, each of which are incorporated by reference.

TaqMan® PCR can be performed using commercially available kits and equipment, such as, for example, ABI PRISM® 7700 Sequence Detection System (Applied Biosystems, Foster City, Calif.), or LightCycler® (Roche Applied Sciences, Mannheim, Germany). In a preferred embodiment, the 5' nuclease assay procedure is run on a real-time quantitative PCR device such as the ABI PRISM® 7700 Sequence Detection System. The system consists of a thermocycler, laser, charge-coupled device (CCD), camera and computer. The system amplifies samples in a 96-well microtiter plate format on a thermocycler. During amplification, laser-induced fluorescent signal is collected in real-time through fiber optics cables for all 96 wells, and detected at the CCD camera. The system includes software for running the instrument and for analyzing the data.

As used herein, a "gene" refers to any segment of DNA associated with a biological function. Thus, genes include coding sequences and optionally, the regulatory sequences required for the expression of the coding sequences.

Nucleic acids are "extended" or "elongated" when additional nucleotides are incorporated into the nucleic acids, for example by a nucleotide incorporating biocatalyst, at the 3' end of a nucleic acid.

A "moiety" or "group" refers to one of the portions into which something, such as a molecule, is divided (e.g., a functional group, substituent group, or the like). For example, a nucleotide typically comprises a base group (e.g., adenine, thymine, cytosine, guanine, uracil, or an analog), a sugar moiety, and one or more phosphate groups.

A "benzyl group" refers a monovalent aromatic group with the formula $C_6H_5CH_2$— and is used interchangeably with the term "phenylmethyl".

A "genotype" refers to all or part of the genetic constitution of a cell or subject, or group of cells or subjects. For example, a genotype includes the particular mutations and/or alleles (e.g. polymorphisms, such as single nucleotide polymorphisms (SNPs) or the like) present at a given locus or distributed in a genome. "Genotyping" refers to an assay that determines the genotype of a cell or subject.

A "nucleotide incorporating biocatalyst" or "nucleotide incorporating enzyme" refers to a catalyst (or enzyme) that catalyzes the incorporation of nucleotides into a nucleic acid. Exemplary nucleotide incorporating enzymes include, DNA polymerases, RNA polymerases, terminal transferases, reverse transcriptases, telomerases and the like.

A "thermostable enzyme" refers to an enzyme that is stable (i.e., resists breakdown or denaturation) and retains sufficient catalytic activity when subjected to elevated temperatures for selected periods of time. For example, a thermostable polymerase retains sufficient activity to effect subsequent primer extension reactions, when subjected to elevated temperatures for the time necessary to denature double-stranded nucleic acids. Heating conditions necessary for nucleic acid denaturation are well known in the art and are exemplified in U.S. Pat. Nos. 4,683,202 and 4,683,195. As used herein, a thermostable polymerase is typically suitable for use in a temperature cycling reaction such as the polymerase chain reaction ("PCR"). The examples of thermostable nucleic acid polymerases include *Thermus aquaticus* Taq DNA polymerase, *Thermus* sp. Z05 polymerase, *Thermus flavus* polymerase, *Thermotoga maritima* polymerases, such as TMA-25 and TMA-30 polymerases, Tth DNA polymerase, and the like.

A "modified enzyme" refers to an enzyme comprising an amino acid polymer in which at least one monomer differs from the reference sequence, such as a native or wild-type form of the enzyme or another modified form of the enzyme. Exemplary modifications include monomer insertions, deletions, and substitutions. Modified enzymes also include chimeric enzymes that have identifiable component sequences (e.g., structural or functional domains, etc.) derived from two or more parents. Also included within the definition of modified enzymes are those comprising chemical modifications of the reference sequence. The examples of modified polymerases include G46E E678G CS5 DNA polymerase, G46E L329A E678G CS5 DNA polymerase, G46E L329A D640G S671F CS5 DNA polymerase, G46E L329A D640G S671F E678G CS5 DNA polymerase, a G46E E678G CS6 DNA polymerase, ΔZ05 polymerase, ΔZ05-Gold polymerase, ΔZ05R polymerase, E615G Taq DNA polymerase, E678G TMA-25 polymerase, E678G TMA-30 polymerase, and the like.

The term "5' to 3' nuclease activity" or "5'-3' nuclease activity" refers to an activity of a nucleic acid polymerase, typically associated with the nucleic acid strand synthesis, whereby nucleotides are removed from the 5' end of nucleic acid strand, e.g., E. coli DNA polymerase I has this activity, whereas the Klenow fragment does not.

A polymerase that "substantially lacks 5'-3' nuclease activity" refers to a polymerase that has 50% or less (e.g., <25%, <20%, <15%, <10%) 5'-3' nuclease activity than Taq DNA polymerase. Methods of measuring 5'-3' nuclease activity and conditions for measurement are well known in the art. See, e.g., U.S. Pat. No. 5,466,591. Examples of DNA polymerases substantially lacking 5' to 3' nuclease activity include the Klenow fragment of E. coli DNA polymerase I; a *Thermus aquaticus* DNA polymerase (Taq) lacking the N-terminal 235 amino acids (e.g., as described in U.S. Pat. No. 5,616,494 and commonly referred to in the art as the "Stoffel fragment"). Other examples include a thermostable DNA polymerase having sufficient deletions (e.g., N-terminal deletions), mutations, or modifications so as to eliminate or inactivate the domain responsible for the 5'-3' nuclease activity. See, e.g., U.S. Pat. No. 5,795,762.

A "label" refers to a moiety attached (covalently or non-covalently), to a molecule and capable of providing information about the molecule. Exemplary labels include fluorescent labels, colorimetric labels, chemiluminescent labels, bioluminescent labels, radioactive labels, mass-modifying groups, antibodies, antigens, biotin, haptens, and enzymes (including peroxidase, phosphatase, etc.).

A "hot start", in the context of a nucleic acid amplification reaction, refers to a protocol, where at least one critical reagent is withheld from the reaction mixture (or, if present in the reaction mixture, the reagent remains inactive) until the temperature is raised sufficiently to provide the necessary hybridization specificity of the primer or primers. A "hot start enzyme" is an enzyme, typically a nucleic acid polymerase, capable of acting as the "withheld" or inactive reagent in a hot start protocol.

The term "reaction mixture" refers to a solution containing reagents necessary to carry out a given reaction. An "amplification reaction mixture", which refers to a solution containing reagents necessary to carry out an amplification reaction, typically contains oligonucleotide primers and a DNA polymerase or ligase in a suitable buffer. A "PCR reaction mixture" typically contains oligonucleotide primers, a thermostable DNA polymerase dNTP's, and a divalent metal cation in a suitable buffer. A reaction mixture is referred to as complete if it contains all reagents necessary to enable the reaction, and incomplete if it contains only a subset of the necessary reagents. It will be understood by one of skill in the art that reaction components are routinely stored as separate solutions, each containing a subset of the total components, for reasons of convenience, storage, stability, or to allow for application-dependent adjustment of the component concentrations, and, that reaction components are combined prior to the reaction to create a complete reaction mixture.

As used herein, the term "kit" is used in reference to a combination of articles that facilitate a process, method, assay, analysis or manipulation of a sample. Kits can contain written instructions describing how to use the kit (e.g., instructions describing the methods of the present invention), chemical reagents or enzymes required for the method, primers and probes, as well as any other components.

The present invention is based on the discovery that certain modified nucleotides, when present on a template nucleic acid, are able to prevent or inhibit the extension of a primer oligonucleotide by DNA polymerase but can still maintain Watson-Crick base pairing with its complementary base on the primer. One such modified nucleotide is the deoxyguanosine analog, $N^2$-benzyl-deoxyguanosine ($N^2$-benzyl-dG) which, as shown on FIG. 1A, contains a benzyl group on the C-2 nitrogen of the exocyclic amino group. The nucleotides with covalent modifications of the exocyclic amino groups have been described in U.S. Pat. No. 6,001,611, which is incorporated herein by reference. The synthesis of such nucleotides, and oligonucleotides incorporating such nucleotides are also described in the '611 patent.

While not being constrained by the theory, it is believed that $N^2$-benzyl-dG is able to prevent primer extension by occupying the minor groove of double-stranded DNA, thereby behaving as a "minor groove binder" and interfering with the active site of the DNA polymerase. Nevertheless, base pairing with a complementary deoxycytosine (dC) nucleotide can still occur as the three hydrogen bonds are not affected by the presence of the benzyl moiety (FIG. 1B).

Therefore, in one aspect, the present invention relates to a method of preventing the extension by DNA polymerase of a primer oligonucleotide that hybridizes to a template nucleotide sequence, comprising incorporating a minor groove binder on the template nucleotide sequence wherein the minor groove binder is a modified nucleotide and the modified nucleotide is $N^2$-benzyl-dG and wherein the primer is incapable of being extended by more than 2 nucleotides beyond the position of the $N^2$-benzyl-dG nucleotide. This method would be applicable for the performance of PCR amplification, nucleic acid sequencing, genotyping, and other applications employing the extension of a primer in a template-dependent manner.

The unique properties of $N^2$-benzyl-dG would also allow for its use in the reduction or prevention of non-specific amplification in a primer-based amplification reaction. It is believed that non-specific amplification occurs when an unstable, transient hybridization duplex is formed between a primer and a non-target molecule, in which the 3' end of the primer is momentarily paired with a complementary base in the other molecule. Initial primer extension results in the formation of complementary sequence which stabilizes the duplex and allows for further extension. U.S. Pat. No. 6,011,611 discloses the use of primers containing modified nucleotides for preventing non-specific amplification that results from the formation of primer-dimers in which the transient hybridization duplex is formed between a primer and another primer. $N^2$-benzyl-dG would not be utilized in a primer to prevent non-specific amplification because its presence in primer extension products which are used as templates in subsequent amplification cycles would cause the termination of primer extension. However, in amplification reactions that utilize a probe (for example a 5' nuclease probe in the Taqman PCR assay) incorporation of $N^2$-benzyl-dG has resulted in reducing or preventing non-specific amplification that results from hybridization taking place between a primer and a probe.

Therefore, in another aspect, the present invention relates to a method of reducing or preventing non-specific amplification of nucleic acid during an amplification reaction comprising providing at least one pair of primer oligonucleotides capable of amplifying a target nucleic acid sequence; providing a probe oligonucleotide that incorporates a minor groove binder that blocks the extension of the primer by a DNA polymerase by more than 2 nucleotides beyond the position of the minor groove binder when the primer hybridizes to the probe oligonucleotide. In one embodiment, the minor groove binder is a modified nucleotide. In another embodiment, the modified nucleotide is $N^2$-benzyl-dG.

In another aspect, the invention provides a reaction mixture for the amplification of nucleic acids, comprising at least one pair of primer oligonucleotides and at least one probe oligonucleotide that incorporates a $N^2$-benzyl-dG nucleotide. In some embodiments, the reaction mixture further comprises the reagents and solutions generally necessary for the amplification of nucleic acids, including a nucleotide-incorporating biocatalyst, nucleic acid precursors, i.e. nucleoside triphosphates, and organic and inorganic ions, suitable for the support of the activity of the nucleotide-incorporating biocatalyst.

In another aspect, the invention provides kits for conducting the amplification reaction according to the invention. The kit generally includes assay-specific components as well as components generally required for performing DNA amplification assays. As the assay-specific components, the amplification kit of the present invention typically includes at least one pair of primer oligonucleotides, at least one probe oligonucleotide that incorporates a $N^2$-benzyl-dG nucleotide, and a set of instructions for conducting the amplification reaction of the present invention. In some embodiments, the kit includes two or more pairs of primer oligonucleotides and two or more probe oligonucleotides wherein each probe oligonucleotide incorporates a $N^2$-benzyl-dG nucleotide. As the components generally required for nucleic acid amplification, the kit of the present invention typically includes one or more of a nucleotide incorporating biocatalyst, nucleic acid precursors, such as nucleoside triphosphates (deoxyribonucleoside triphosphates or ribonucleoside triphosphates), optionally, a pyrophosphatase, for minimizing pyrophosphorolysis of nucleic acids, a uracil N-glycosylase (UNG) for protection against carry-over contamination of amplification reactions, and pre-made reagents and buffers necessary for the amplification reaction and detection.

The following examples and figures are provided to aid the understanding of the present invention, the true scope of which is set forth in the appended claims. It is understood that modifications can be made in the procedures set forth without departing from the spirit of the invention.

EXAMPLES

Example 1

Primer Extension

Figure 2:
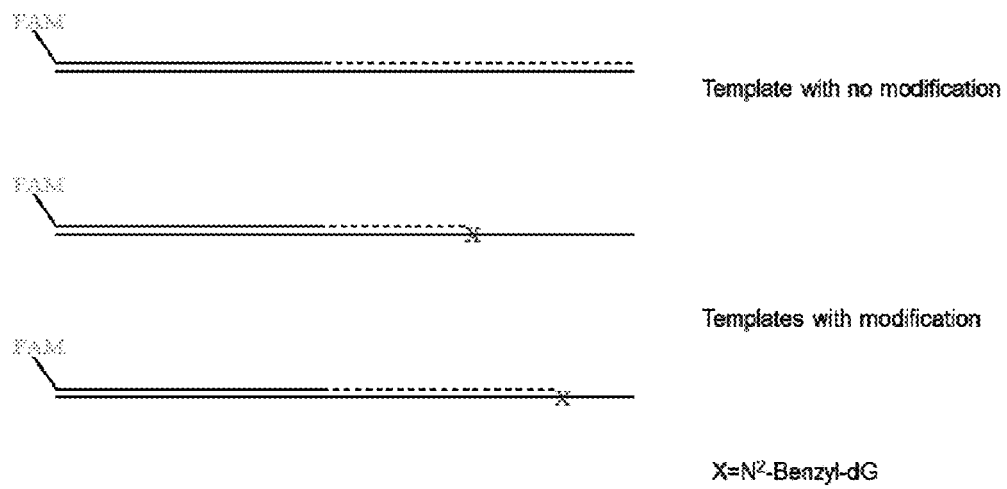
FIG. 2 is a graphic representation of the blocking of primer extension using a template nucleic acid containing $N^2$-benzyl-dG.

In order to demonstrate that a template nucleic acid containing $N^2$-benzyl-dG is able to block the extension of a primer by DNA polymerase as graphically depicted in FIG. 2, a primer extension experiment was set up using a FAM-labeled primer oligonucleotide and three complementary template oligonucleotides with sequences that are shown below:

```
NJS01 FAM-
                                        (SEQ ID NO: 1)
CCCTCGCAGCCGTCCAACCAACTCA

NJS03
                                        (SEQ ID NO: 2)
GGGAGCGTCGGCAGGTTGGTTGAGTAGGTCTTGTTT

NJS339-1A
                                        (SEQ ID NO: 3)
CGGAGCGTCGGCAGGTTGGTTGAGTAGETCTTGTTT

NJS339-2A
                                        (SEQ ID NO: 4)
CGGAGCGTCGGCAGGTTGGTTGAGTAGGTCTTETTT
(E = N2-benzyl-dG)
```

Each primer extension reaction (50 µl) contained 50 nM primer and 75 nM template oligonucleotide, with 15 units (20 nM) Z05D DNA polymerase, 337.5 µM each dATP, dCTP, dGTP, dUTP, 50 mM Tricine (pH 8.0), 100 mM potassium acetate (pH 7.0), 3 mM manganese acetate, 4% glycerol, 5% DMSO, 0.01% Tween-20. Primer extension with Z05D DNA polymerase was performed at 60° C. and the reaction was terminated by the addition of EDTA at various time points. The primer extension products were diluted into loading buffer with formamide and were analyzed by capillary electrophoresis (ABI PRISM® 3100 Genetic Analyzer) in the presence of labeled size standards.

Figure 3:
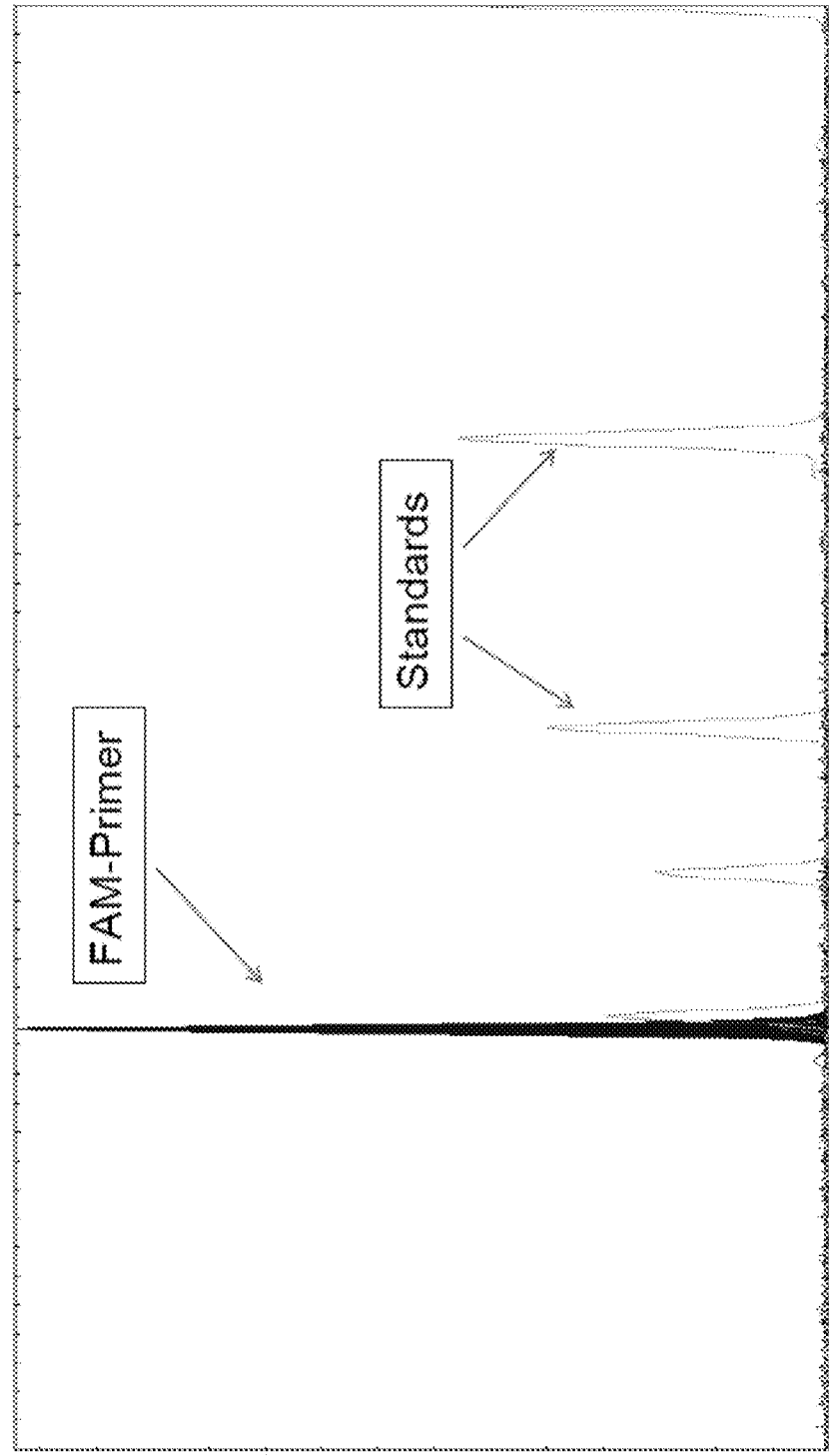
FIG. 3 shows the results of the primer extension reaction of Example 1 with A) No Enzyme, 0 min—Control Template, B) No Enzyme, 0 min—NJS339_1 Template, C) No Enzyme, 0 min—NJS339_2A Template, D) 5 min extension—Control Template, E) 5 min extension—NJS339_1A Template, F) 5 min extension—NJS339_2A Template.
Figure 3:
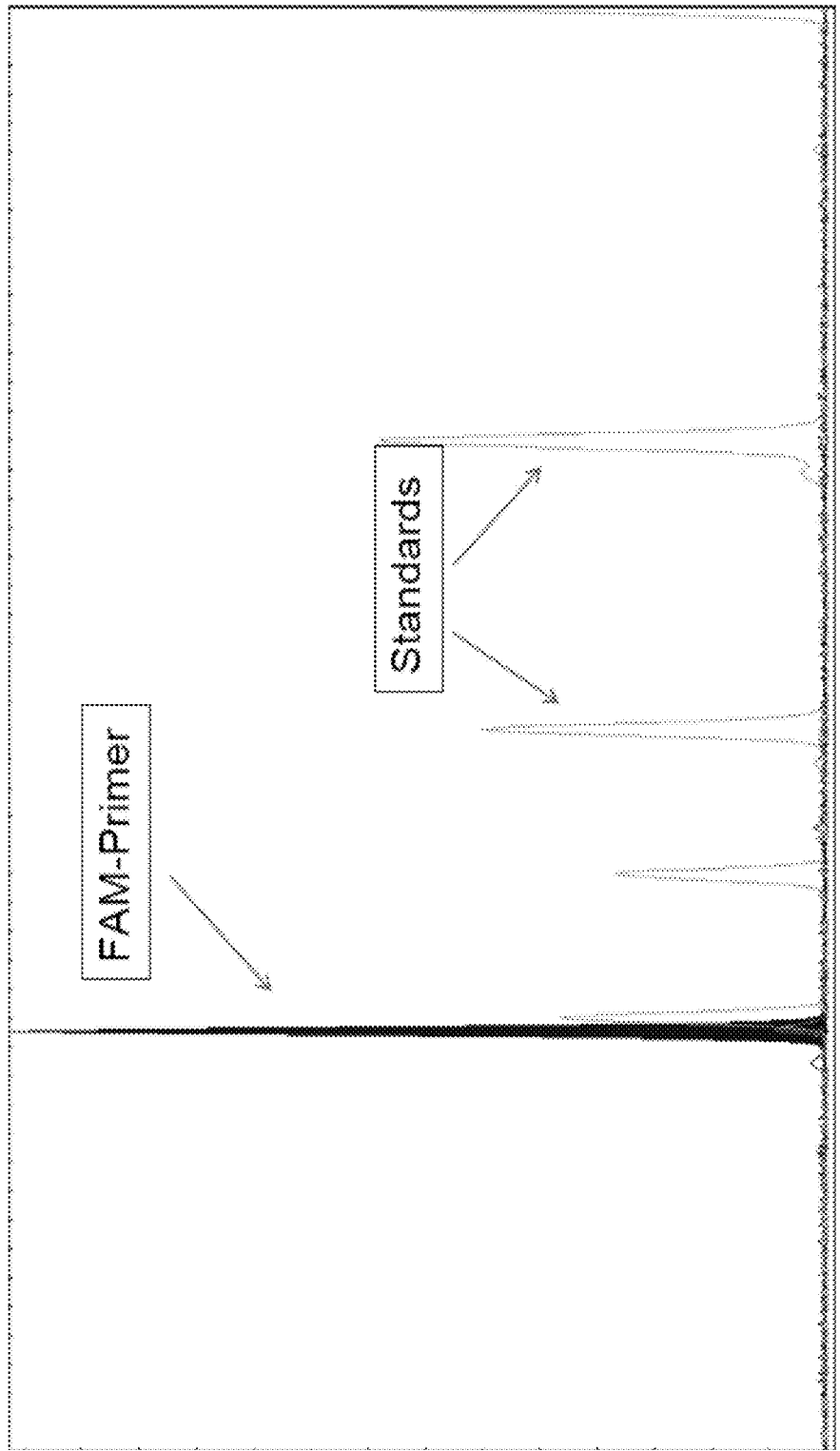
Figure 3:
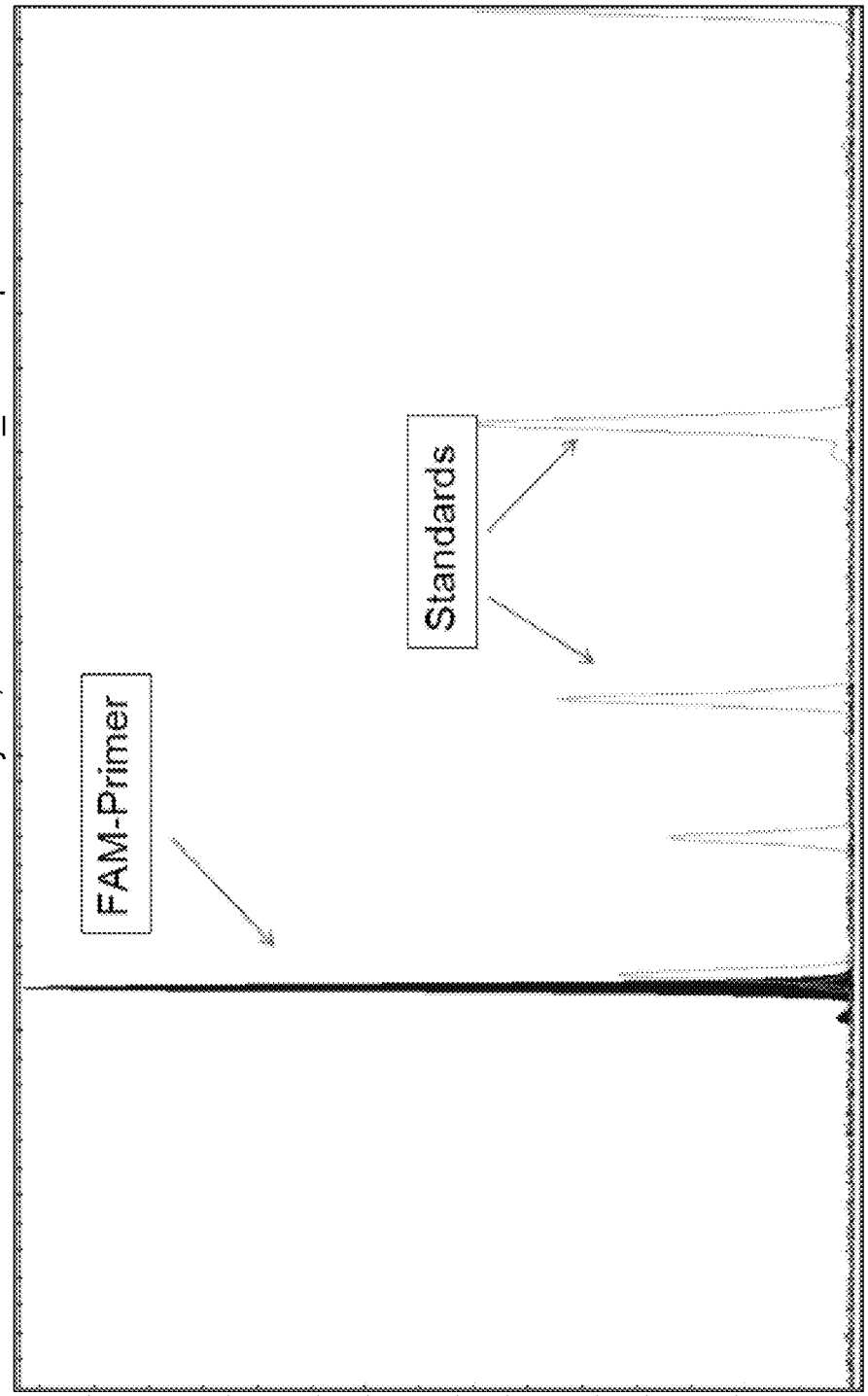
Figure 3:
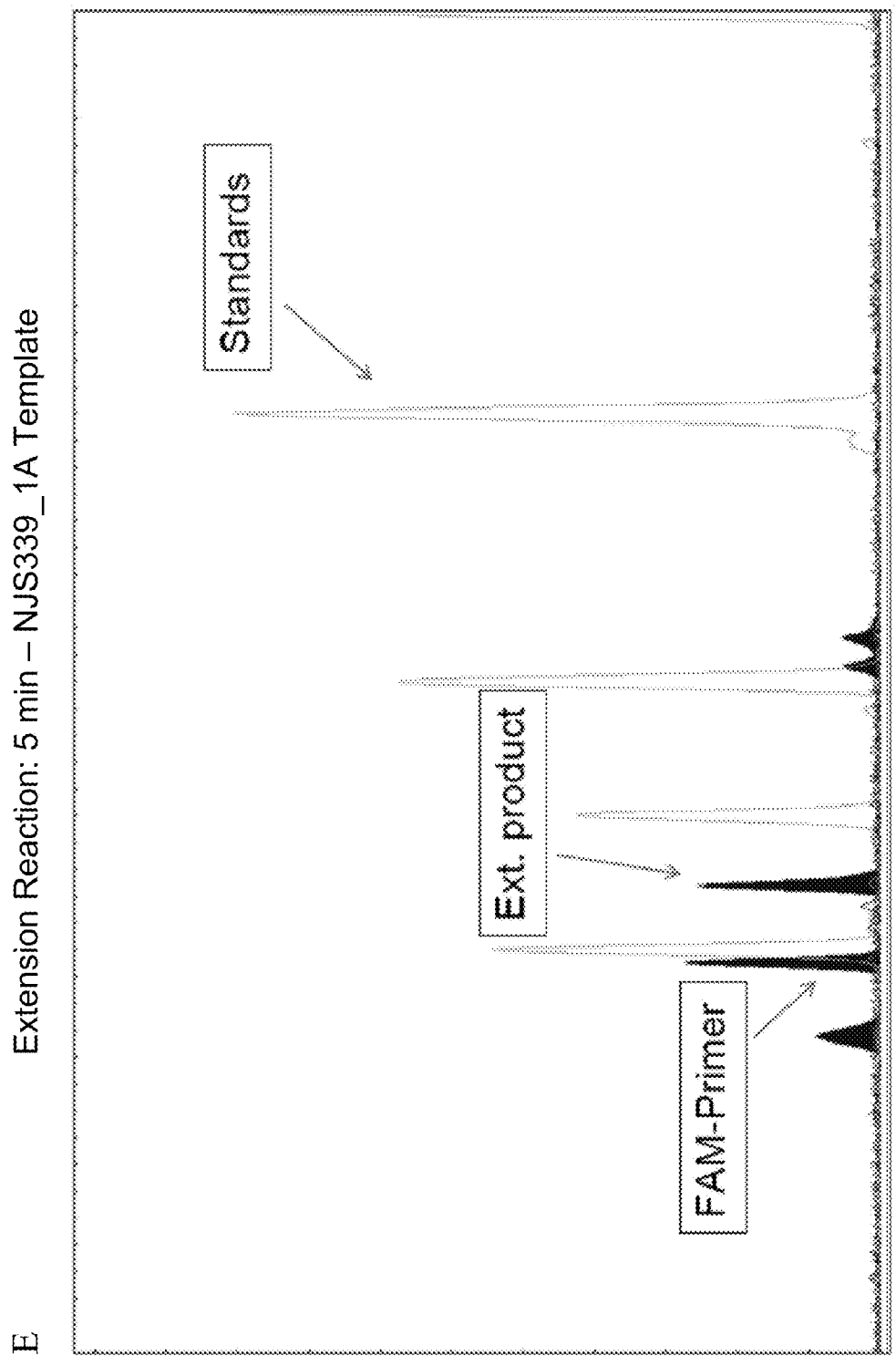
Figure 3:
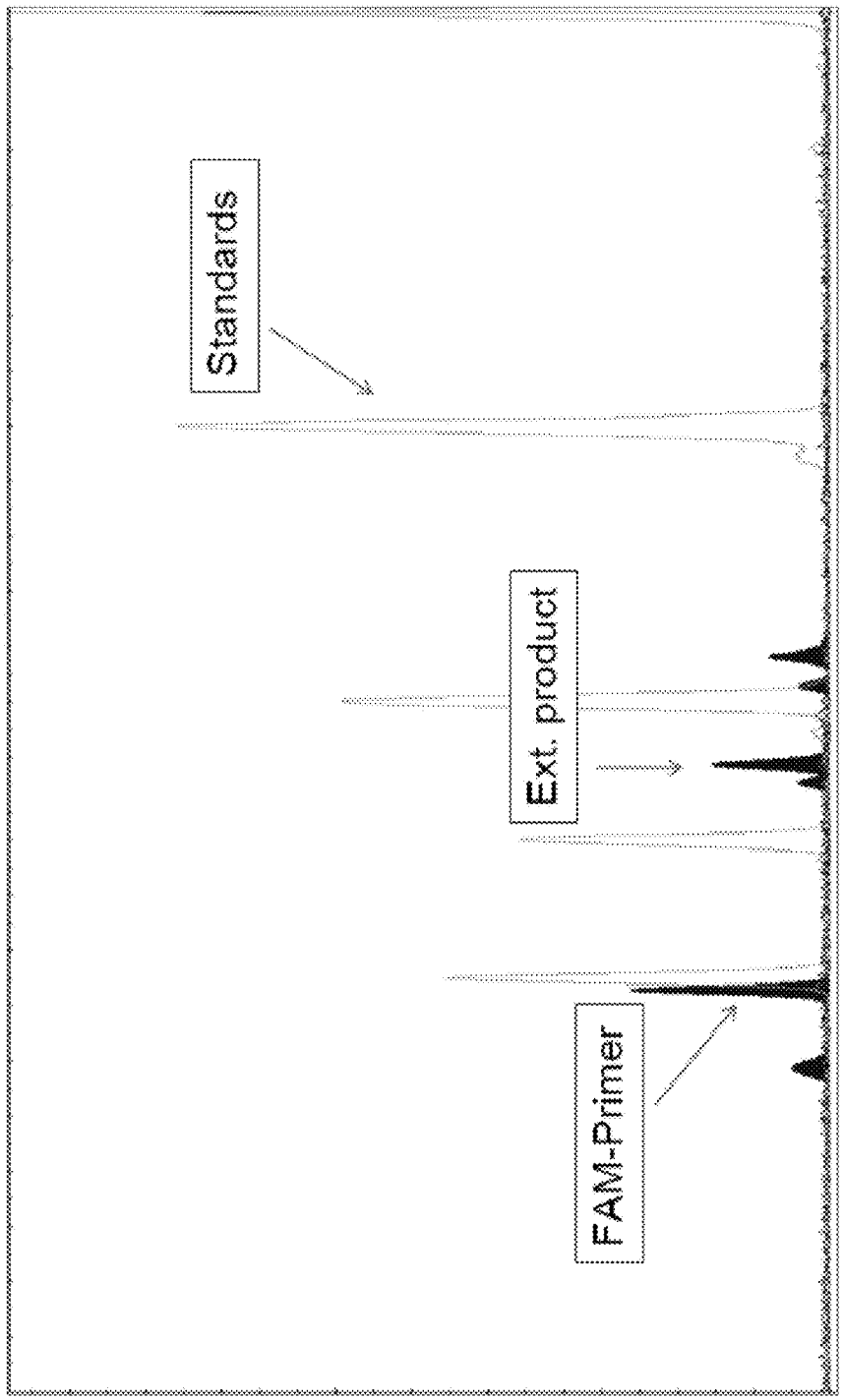

The results are shown on FIG. 3. The extension products from the templates that contain $N^2$-benzyl-dG are clearly smaller than the extension product from the control template. This indicates that a template nucleic acid that contains a $N^2$-benzyl-dG residue can stop or dramatically reduce the extension rate of a primer by DNA polymerase.

Example 2

Duplex Stability

To study the effect of $N^2$-benzyl-dG on hybridization, a melting temperature experiment was performed using an unmodified complement oligonucleotide and three test oligonucleotides. The three test oligonucleotides for which melting temperatures were determined represent (a) an unmodified control oligonucleotide, (b) an oligonucleotide with identical sequence as (a) with $N^2$-benzyl-dG at the N-9 position, and (c) an oligonucleotide with identical sequence as (a) with $N^2$-benzyl-dG at the N-4 position. The nucleotide sequences of these oligonucleotides are as follows:

```
Complement
                                        (SEQ ID NO: 5)
3'-AAACAAGACCTACTCAACCAACCTGCCGACGCTCCG Test Control
                                        (SEQ ID NO: 6)
5'-TTTGTTCTGGATGAGTTGGTTGGACGGCTGCGAGGC Test N-9
                                        (SEQ ID NO: 7)
5'-TTTGTTCTEGATGAGTTGGTTGGACGGCTGCGAGGC Test N-4
                                        (SEQ ID NO: 8)
5'-TTTETTCTGGATGAGTTGGTTGGACGGCTGCGAGGC
```

The experimental conditions were as follows. Each reaction was prepared in 50 µl volume and in replicates of two and contained 40 pmol of each test oligonucleotide and 40 pmol of complement oligonucleotide, in a buffer that contained 90 mM potassium acetate (pH 7.0), 50 mM Tricine (pH 8.3), 3 mM manganous acetate, 3% glycerol, 5% DMSO, 300 µM each of dATP, dCTP, dGTP and 600 µM dUTP. The melting temperature for the hybridization duplex formed between each test oligonucleotide and the complement oligonucleotide was determined using the LighCycler® 480 Instrument under the following conditions. Each reaction well as first heated to 91° C. and rapidly cooled to 40° C. to allow annealing to take place. Temperature was then continuously raised at a ramp rate of 0.06° C./sec to 90° C. Detection of DNA duplex melting was via the change in fluorescence by the double-stranded DNA-binding dye Syto-13 (final concentration 100 µM).

Figure 4:
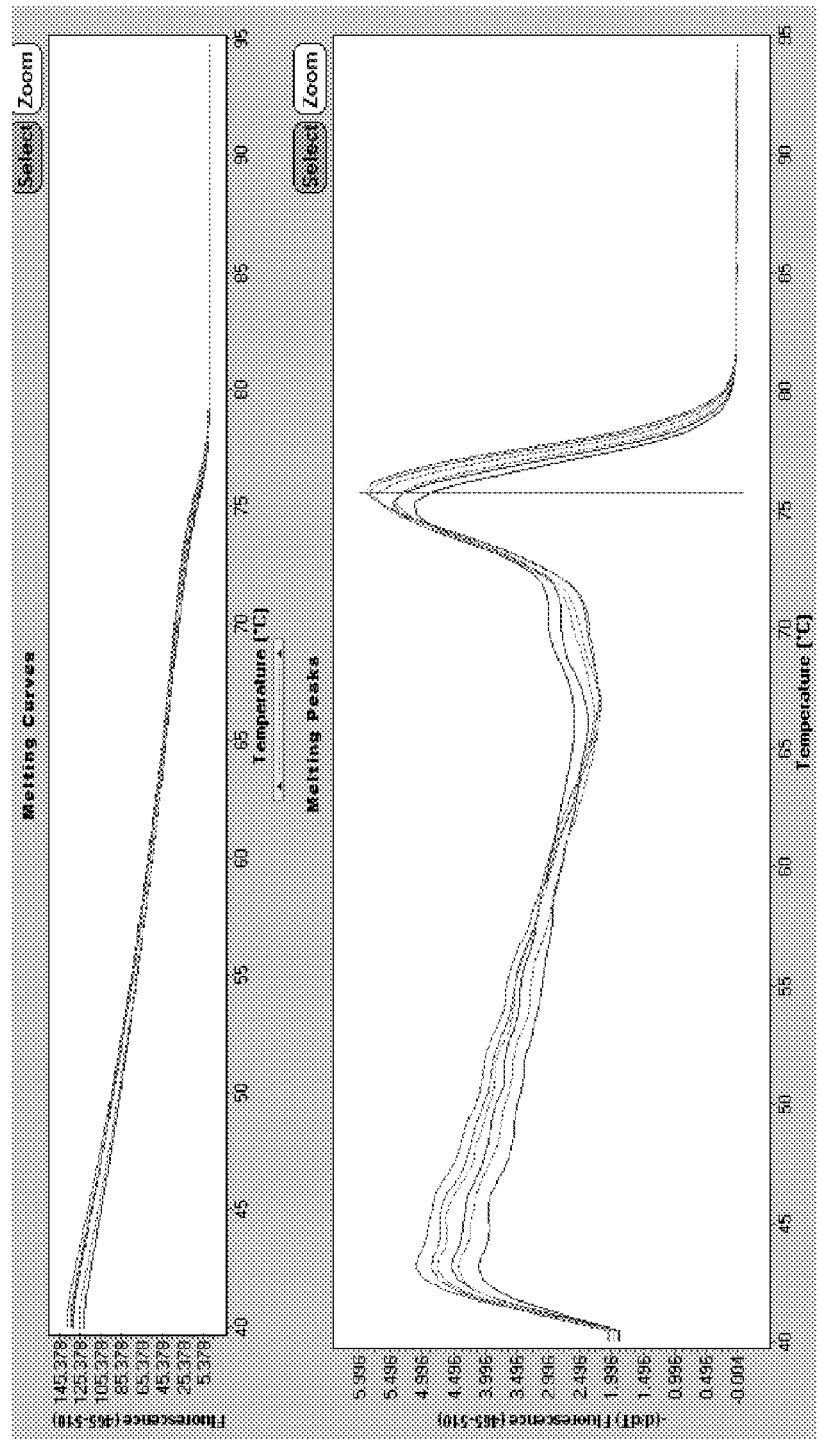
FIG. 4 shows the melting temperatures of a complement oligonucleotide against three test oligonucleotides, one unmodified control oligonucleotide and two oligonucleotides with the identical sequence as the control oligonucleotide but with $N^2$-benzyl-dG modification at the N-4 or N-9 position.

The results of the experiment are shown on FIG. 4 with the top panel showing absolute fluorescence plotted as a function of temperature and the bottom panel depicting the same melting curve data but displaying the data as a first derivative plot (as a function of temperature). Only a small melting temperature difference was observed between the control oligonucleotide and the oligonucleotides containing $N^2$-benzyl-dG with ΔTm values of 0.3° C.-0.5° C. Thus the presence of $N^2$-benzyl-dG in an oligonucleotide does not lead to significant destabilization of a hybridization duplex formed between the $N^2$-benzyl-dG-containing oligonucleotide and a complementary nucleic acid sequence. This experiment demonstrates that $N^2$-benzyl-dG can be incorporated within a probe oligonucleotide (e.g. a TaqMan® probe) without adversely affecting the hybridization property of the probe.

Example 3

Cleavage Efficiency

To investigate whether a 5'-nuclease oligonucleotide probe that contains $N^2$-benzyl-dG can be effectively cleaved by the 5' to 3' nuclease activity of DNA polymerase in a TaqMan® PCR assay, the following experiment was performed. Taq-Man® probes that target specific viral sequences in HIV-1, HIV-2, HBV, and HCV were modified to contain one residue of $N^2$-benzyl-dG. Each of the modified TaqMan® probes was then compared with its counterpart unmodified TaqMan® probe in a standard kinetic PCR assay using target-specific primers and Z05 DNA polymerase for its amplicon-detection ability which indicates how effectively the probe are cleaved by the 5' to 3' nuclease activity of the DNA polymerase.

Figure 5:
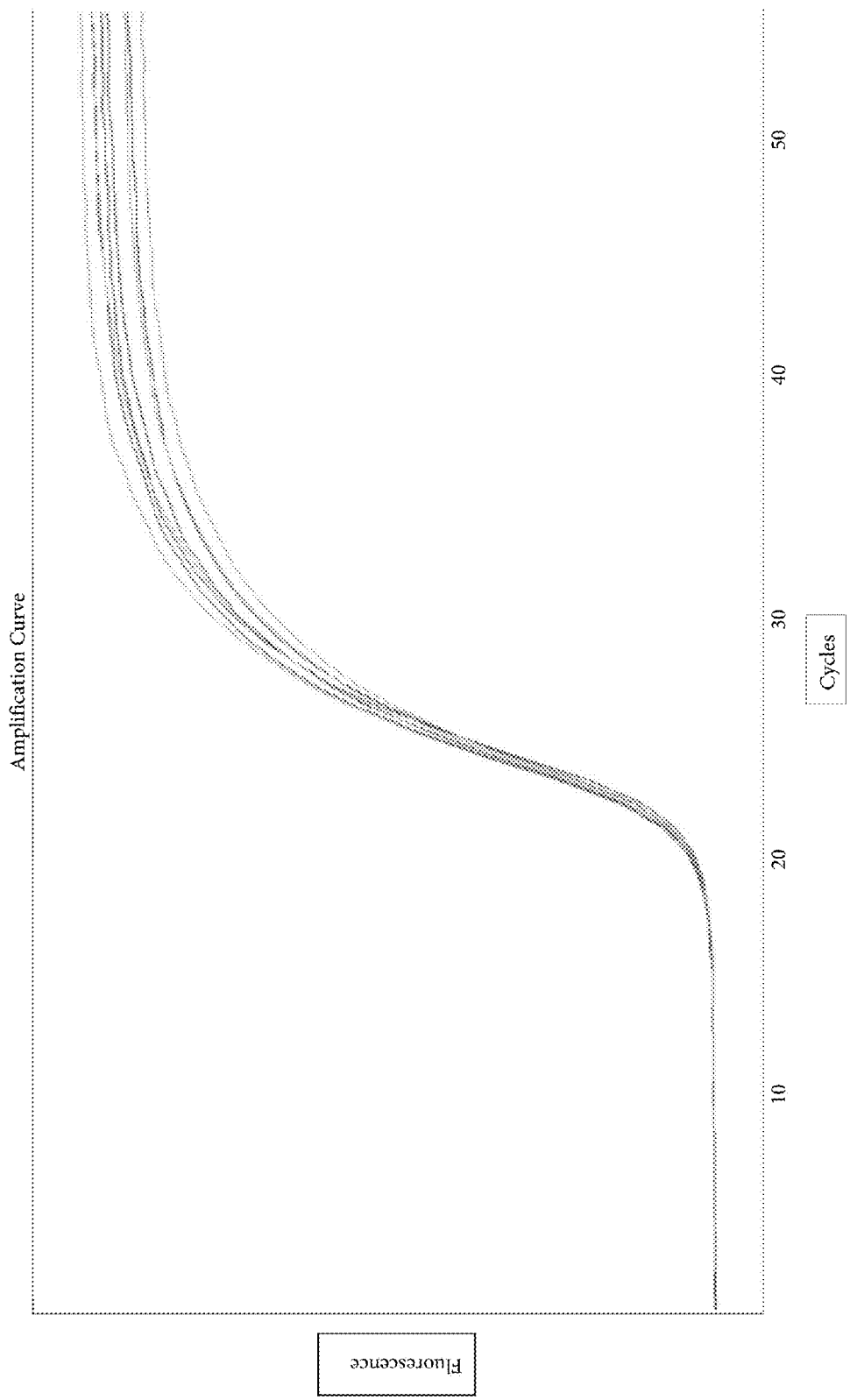
FIG. 5 shows the cleavage efficiency of $N^2$-benzyl-dG residue containing TaqMan® probes compared to unmodified TaqMan® probes with the identical sequence where each probe targets the sequence from: A) HIV-1, B) HBV, C) HCV, D) HIV-2, and E) internal standard.
Figure 5:
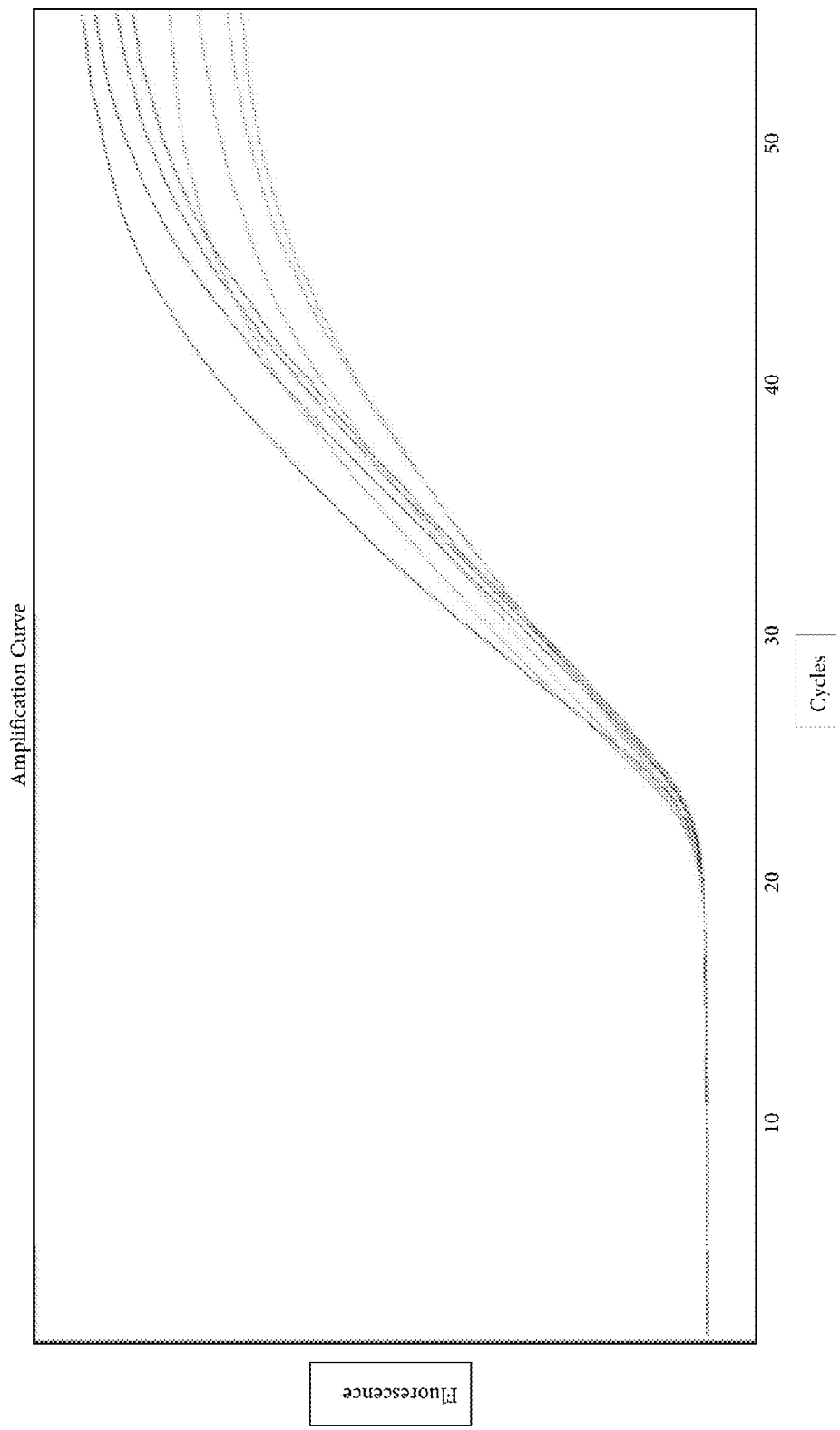
Figure 5:
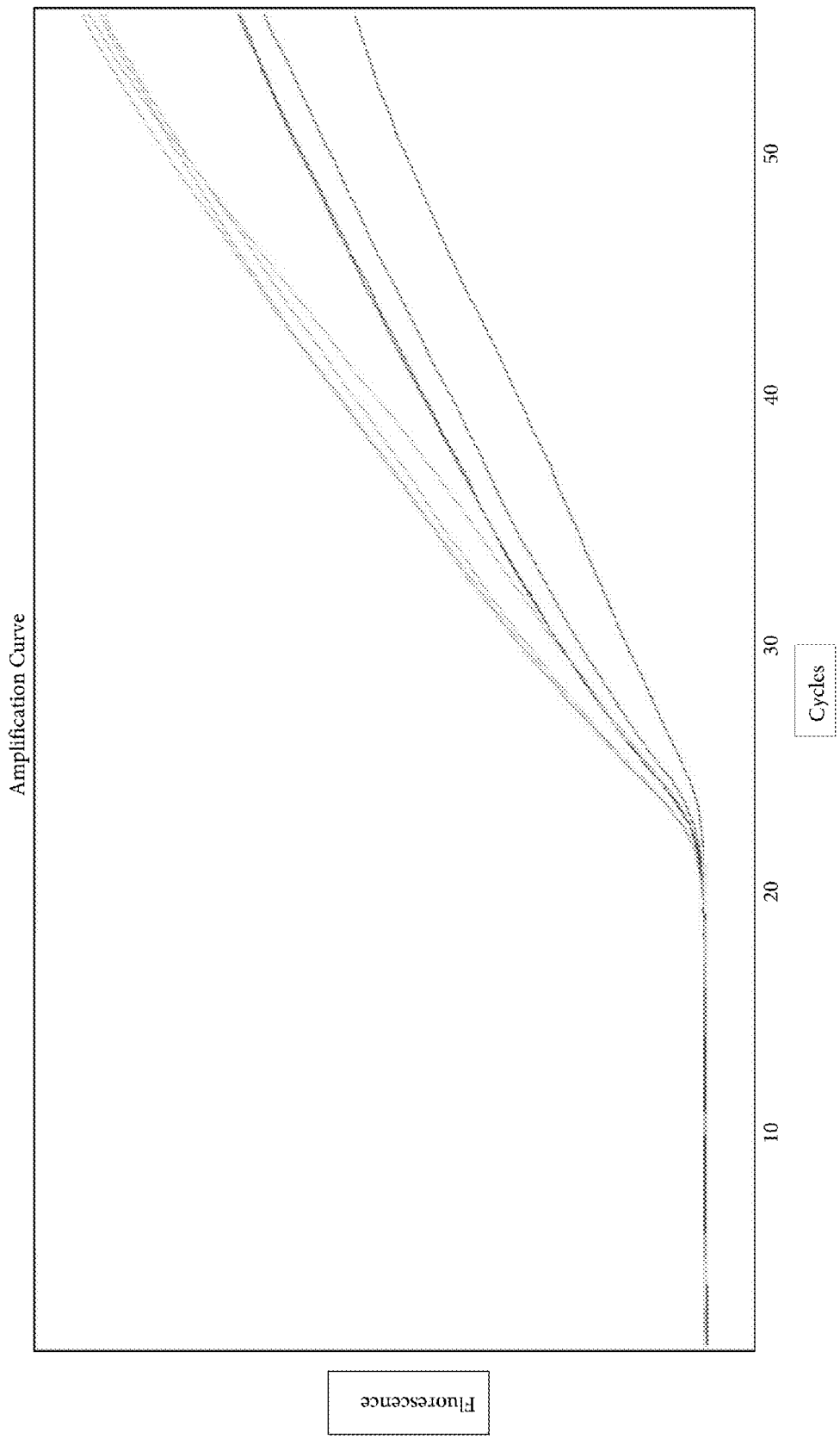
Figure 5:
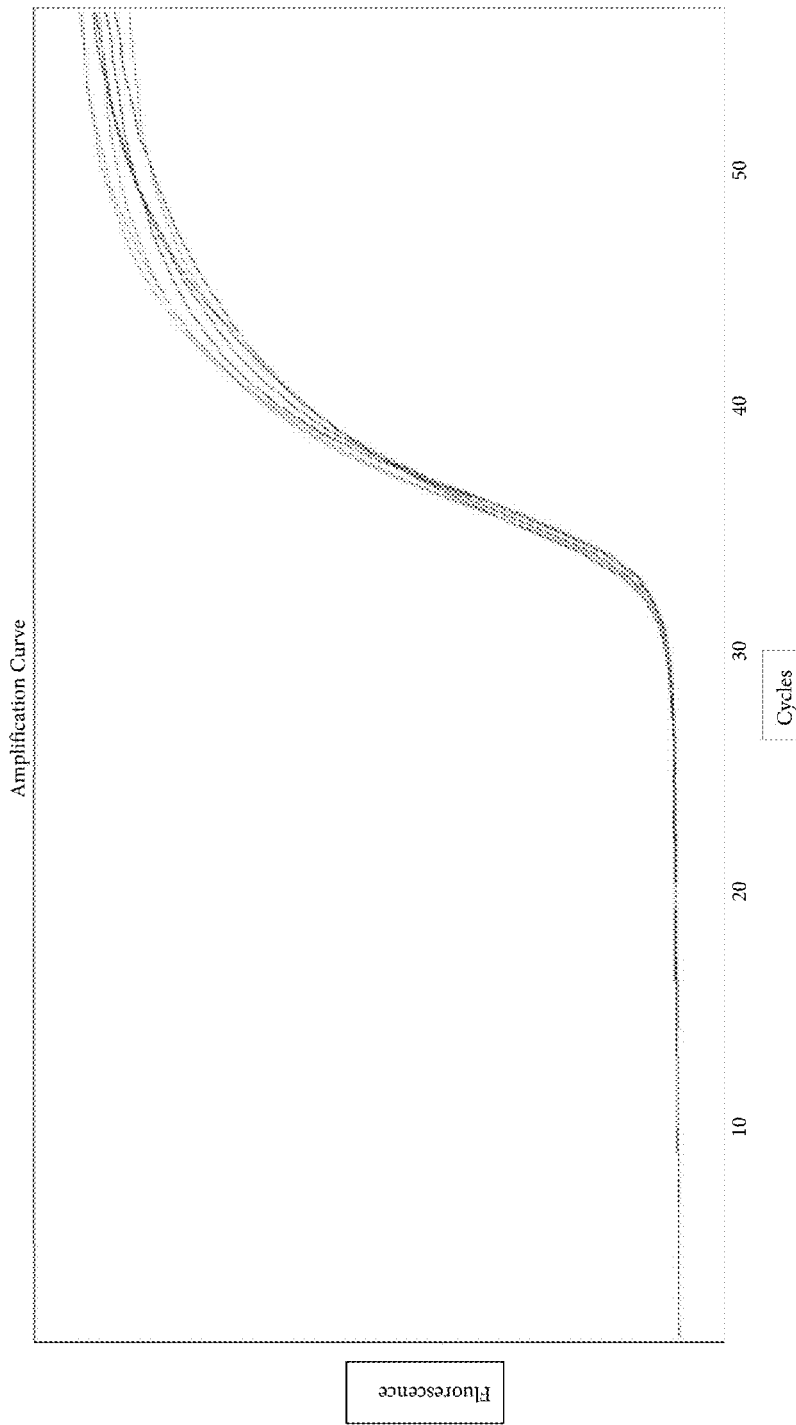

The results are shown on FIG. 5 as represented by growth curves for each PCR reaction with fluorescence plotted against PCR cycle number. For each target, there is little or no difference between the growth curves generated using $N^2$-benzyl-dG-modified TaqMan® probes and those using unmodified TaqMan® probes. This demonstrates that the cleavage efficiency by DNA polymerase of $N^2$-benzyl-dG containing TaqMan® probes is the same as that of a Taq-Man® probe that does not contain $N^2$-benzyl-dG.

Example 4

Reduction of False Positives

During a multiplex PCR assay, it was observed that false positive data as a result of non-specific amplification appeared in a channel that contained a HCV-specific Taq-Man® probe labeled with the fluorescent JA270 dye. As shown in Table 1, incorporation of $N^2$-benzyl-dG in the HCV TaqMan® probe was able to eliminate the presence of the false positive signal in the JA270 channel (Channel 3).

TABLE 1

| Samples | | | Unexpected Reactives (False Positives) | |
|---|---|---|---|---|
| Summary | Matrix | Replicates | Channel 3 | Overall |
| Control Probes | NHP | 120 | 3 | 3% |
| Benzyl-dG probes | NHP | 120 | 0 | 0% |

Example 5

Reduction of False Positives in a Multiplex PCR Assay

In order to show the potential of $N^2$-benzyl-dG modification of TaqMan® probes as a means to reduce false positivity, an experiment was run in which the false positivity rate was measured using conventional probes and those with $N^2$-benzyl-dG at specific locations within the probe sequences. Since false positivity is relatively infrequent in highly optimized amplification systems, a modified PCR Master Mix was developed which favored the generation of non-specific amplification products. In this model system, a high level of false positivity could be induced such that a statistically significant difference between the rates would be obvious from a relatively limited number of input samples.

Samples of Normal Human Plasma (NHP, 850 µl each, N=388 for each condition tested) which had been previously confirmed as being negative for the viruses to be detected, Human Immunodeficiency Virus (HIV), Hepatitis C Virus (HCV), and Hepatitis B Virus (HBV), were processed using an automated DNA preparation and amplification system (Roche Pilot System). Eluates from each sample that had undergone the sample preparation system were collected and distributed (25 µl in each well) into amplification plates for real-time PCR detection using TaqMan® probes. 25 µl of an activated Master Mix (6.6 mM manganese acetate pH 6.1, 0.036 µM sodium acetate, 10.8% DMSO, 0.054 µM sodium acetate pH 7.0, 240 mM potassium acetate pH 7.0, 6% glycerol, 120 mM Tricine pH 8.0, 0.4 U/µL UNG, 800 µM dGTP, 800 µM dATP, 800 µM dCTP, 1600 µM dUTP, 1.8 U/µL Z05-D DNA Polymerase) containing forward and reverse primers and TaqMan® probes with or without $N^2$-benzyl-dG was then added to bring the final reaction volume to 50 µl and the plates were sealed and introduced into the thermocycler. The thermocycling profile was conducted as shown below in Table 2.

TABLE 2

| | Mode | Temperature (C°) | Acquisition Mode | Plateau (hh:mm:ss) | Measurement (hh:mm:ss) | Ramp Rate (° C./s) | Cycles |
|---|---|---|---|---|---|---|---|
| Pre-PCR | UNG-Step | 50 | — | 00:02:00 | 00:00:00 | 2.2 | 1 |
| | UNG/Template Denaturating | 94 | — | 00:00:05 | 00:00:00 | 4.4 | |
| | RT-Step | 55 | — | 00:02:00 | 00:00:00 | 2.2 | |

TABLE 2-continued

| Mode | Temperature (C°) | Acquisition Mode | Plateau (hh:mm:ss) | Measurement (hh:mm:ss) | Ramp Rate (° C./s) | Cycles |
|---|---|---|---|---|---|---|
| | 60 | — | 00:06:00 | 00:00:00 | 4.4 | |
| | 65 | — | 00:04:00 | 00:00:00 | 4.4 | |
| 1. Measurement | 95 | — | 00:00:05 | 00:00:00 | 4.4 | 5 |
| | 55 | Single | 00:00:30 | 00:00:08 | 2.2 | |
| 2. Measurement | 91 | — | 00:00:05 | 00:00:00 | 4.4 | 45 |
| | 58 | Single | 00:00:25 | 00:00:08 | 2.2 | |
| Cooling | 40 | — | 00:02:00 | 00:00:00 | 2.2 | 1 |

Forward and reverse primer sequences used in the experiment ranged in final concentration between 0.125 µM and 0.3 µM and they were selected from the following. SEQ ID NO: 9 to 24 for HIV Type 1 (HIV-1) GAG; SEQ ID NO: 25 to 32 for HIV-1 LTR; SEQ ID NO: 33 to 35 for HIV Type 2 (HIV-2); SEQ ID NO: 36 and 37 for HBV; SEQ ID NO: 38-59 for HCV.

TaqMan® probe sequences used in the experiment ranged in final concentration between 0.15 µM and 0.3 µM and they were selected from the following. SEQ ID NO: 60 to 64 for HIV-1 GAG; SEQ ID NO: 65 and 66 for HIV-1 LTR; SEQ ID NO: 67 for HIV-2; SEQ ID NO: 68 for HBV; SEQ ID NO: 69-76 for HCV. All the probes were labeled at the 5' terminus by a fluorescent dye: FAM for the HIV (both HIV-1 and HIV-2) probes, HEX for the HBV probe, and JA270 for the HCV probe, and contained an internal BHQ-2 quencher molecule.

For TaqMan® probes that contained the $N^2$-benzyl-dG modified nucleotide, an internal deoxyguanosine residue, located approximately in a position that is the middle of the probe was modified from dG to $N^2$-benzyl-dG. For example, in the HIV-2 probe (SEQ ID NO: 67), the dG residue at position 12 from the 5' terminus was converted to $N^2$-benzyl-dG. Similarly for the HBV probe (SEQ ID NO: 68), $N^2$-benzyl-dG was placed at position 20 from the 5' terminus.

The results of the experiment described above for the false positivity reduction by $N^2$-benzyl-dG are as follows. In the assays using conventional probes (i.e. without $N^2$-benzyl-dG), no FAM signal (for detection of HIV-1 and HIV-2), one HEX signal (for detection of HBV) and 39 JA270 signals (for detection of HCV) were detected out of the 388 samples. This lead to a false positivity rate of 10.3% and a specificity of 348/388 or 89.7%. In the assays using $N^2$-benzyl-dG probes, no FAM signal, one HEX signal and 19 JA270 signals were detected, leading to a false positivity rate of 5.15% and a specificity of 368/388 or 94.85%. Therefore, incorporation of $N^2$-benzyl-dG in the HCV TaqMan® probe resulted in a 50% reduction of the false positive signal in the JA270 channel.

While the invention has been described in detail with reference to specific examples, it will be apparent to one skilled in the art that various modifications can be made within the scope of this invention. Thus the scope of the invention should not be limited by any of the examples described herein, but by the claims presented below.

All publications including patent applications and patents cited in this application are incorporated by reference in their entirety for all purposes to the same extent as if each individual publication were individually indicated to be incorporated by reference for all purposes.

The invention claimed is:

1. A reaction mixture for the amplification of three or more target nucleic acids, comprising three or more pairs of primer oligonucleotides and three or more probe oligonucleotides wherein at least one probe oligonucleotide incorporates a N2-benzyl-dG nucleotide.

2. The reaction mixture of claim 1 further comprising a nucleotide-incorporating biocatalyst, nucleoside triphosphates, and a buffer suitable for the amplification of said three or more target nucleic acids by the nucleotide-incorporating biocatalyst.

3. A kit for the amplification of three or more target nucleic acids, comprising three or more pairs of primer oligonucleotides, and three or more probe oligonucleotides wherein at least one probe oligonucleotide incorporates a N2-benzyl-dG nucleotide, at least one nucleotide-incorporating biocatalyst, nucleoside triphosphates, a buffer suitable for the amplification of said three or more target nucleic acids by the at least one nucleotide-incorporating biocatalyst, and a set of instructions for performing the amplification of nucleic acids.

* * * * *

SEQUENCE LISTING

```
<160> NUMBER OF SEQ ID NOS: 76

<210> SEQ ID NO 1
<211> LENGTH: 25
<212> TYPE: DNA
<213> ORGANISM: Artificial Sequence
<220> FEATURE:
<223> OTHER INFORMATION: Primer sequence NJS01

<400> SEQUENCE: 1
ccctcgcagc cgtccaacca actca                                           25

<210> SEQ ID NO 2
<211> LENGTH: 36
<212> TYPE: DNA
<213> ORGANISM: Artificial Sequence
<220> FEATURE:
<223> OTHER INFORMATION: Template Sequence NJS03

<400> SEQUENCE: 2
gggagcgtcg gcaggttggt tgagtaggtc ttgttt                               36

<210> SEQ ID NO 3
<211> LENGTH: 36
<212> TYPE: DNA
<213> ORGANISM: Artificial Sequence
<220> FEATURE:
<223> OTHER INFORMATION: Template Sequence NJS339-1A
```

```
<220> FEATURE:
<221> NAME/KEY: modified_base
<222> LOCATION: (28)..(28)
<223> OTHER INFORMATION: N2-benzyl-dG

<400> SEQUENCE: 3
cggagcgtcg gcaggttggt tgagtaggtc ttgttt                36

<210> SEQ ID NO 4
<211> LENGTH: 36
<212> TYPE: DNA
<213> ORGANISM: Artificial Sequence
<220> FEATURE:
<223> OTHER INFORMATION: Template Sequence NJS339-2A
<220> FEATURE:
<221> NAME/KEY: modified_base
<222> LOCATION: (33)..(33)
<223> OTHER INFORMATION: N2-benzyl-dG

<400> SEQUENCE: 4
cggagcgtcg gcaggttggt tgagtaggtc ttgttt                36

<210> SEQ ID NO 5
<211> LENGTH: 36
<212> TYPE: DNA
<213> ORGANISM: Artificial Sequence
<220> FEATURE:
<223> OTHER INFORMATION: Complement Sequence

<400> SEQUENCE: 5
aaacaagacc tactcaacca acctgccgac gctccg                36

<210> SEQ ID NO 6
<211> LENGTH: 36
<212> TYPE: DNA
<213> ORGANISM: Artificial Sequence
<220> FEATURE:
<223> OTHER INFORMATION: Test Sequence Control

<400> SEQUENCE: 6
tttgttctgg atgagttggt tggacggctg cgaggc                36

<210> SEQ ID NO 7
<211> LENGTH: 36
<212> TYPE: DNA
<213> ORGANISM: Artificial Sequence
<220> FEATURE:
<223> OTHER INFORMATION: Test Sequence N-9
<220> FEATURE:
<221> NAME/KEY: modified_base
<222> LOCATION: (9)..(9)
<223> OTHER INFORMATION: N2-benzyl-dG

<400> SEQUENCE: 7
tttgttctgg atgagttggt tggacggctg cgaggc                36

<210> SEQ ID NO 8
<211> LENGTH: 36
<212> TYPE: DNA
<213> ORGANISM: Artificial Sequence
<220> FEATURE:
<223> OTHER INFORMATION: Test Sequence N-4
<220> FEATURE:
<221> NAME/KEY: modified_base
<222> LOCATION: (4)..(4)
<223> OTHER INFORMATION: N2-benzyl-dG

<400> SEQUENCE: 8
```

```
tttgttctgg atgagttggt tggacggctg cgaggc                               36

<210> SEQ ID NO 9
<211> LENGTH: 29
<212> TYPE: DNA
<213> ORGANISM: Artificial Sequence
<220> FEATURE:
<223> OTHER INFORMATION: HIV-1 primer

<400> SEQUENCE: 9
agtgggggga catcaagcag ccatgcaaa                                      29

<210> SEQ ID NO 10
<211> LENGTH: 30
<212> TYPE: DNA
<213> ORGANISM: Artificial Sequence
<220> FEATURE:
<223> OTHER INFORMATION: HIV-1 primer

<400> SEQUENCE: 10
agtgggggga catcaagcag ccatgcaaat                                     30

<210> SEQ ID NO 11
<211> LENGTH: 23
<212> TYPE: DNA
<213> ORGANISM: Artificial Sequence
<220> FEATURE:
<223> OTHER INFORMATION: HIV-1 primer

<400> SEQUENCE: 11
gctttcagcc cagaagtaat acc                                            23

<210> SEQ ID NO 12
<211> LENGTH: 25
<212> TYPE: DNA
<213> ORGANISM: Artificial Sequence
<220> FEATURE:
<223> OTHER INFORMATION: HIV-1 primer

<400> SEQUENCE: 12
ggacacatca agcagccatg caaat                                          25

<210> SEQ ID NO 13
<211> LENGTH: 20
<212> TYPE: DNA
<213> ORGANISM: Artificial Sequence
<220> FEATURE:
<223> OTHER INFORMATION: HIV-1 primer

<400> SEQUENCE: 13
agagaaccaa ggggaagtga                                                20

<210> SEQ ID NO 14
<211> LENGTH: 28
<212> TYPE: DNA
<213> ORGANISM: Artificial Sequence
<220> FEATURE:
<223> OTHER INFORMATION: HIV-1 primer

<400> SEQUENCE: 14
ataatccacc tatcccagta ggagaaat                                       28

<210> SEQ ID NO 15
<211> LENGTH: 29
<212> TYPE: DNA
<213> ORGANISM: Artificial Sequence
```

```
<220> FEATURE:
<223> OTHER INFORMATION: HIV-1 primer

<400> SEQUENCE: 15
agtgggggga caccaggcag caatgcaaa                              29

<210> SEQ ID NO 16
<211> LENGTH: 20
<212> TYPE: DNA
<213> ORGANISM: Artificial Sequence
<220> FEATURE:
<223> OTHER INFORMATION: HIV-1 primer

<400> SEQUENCE: 16
catagcagga actactagta                                        20

<210> SEQ ID NO 17
<211> LENGTH: 30
<212> TYPE: DNA
<213> ORGANISM: Artificial Sequence
<220> FEATURE:
<223> OTHER INFORMATION: HIV-1 primer

<400> SEQUENCE: 17
ggtactagta gttcctgcta tgtcacttcc                             30

<210> SEQ ID NO 18
<211> LENGTH: 25
<212> TYPE: DNA
<213> ORGANISM: Artificial Sequence
<220> FEATURE:
<223> OTHER INFORMATION: HIV-1 primer

<400> SEQUENCE: 18
ctatgtcact tccccttggt tctct                                  25

<210> SEQ ID NO 19
<211> LENGTH: 30
<212> TYPE: DNA
<213> ORGANISM: Artificial Sequence
<220> FEATURE:
<223> OTHER INFORMATION: HIV-1 primer

<400> SEQUENCE: 19
ggtactagta gttcctgcta tatcacttcc                             30

<210> SEQ ID NO 20
<211> LENGTH: 20
<212> TYPE: DNA
<213> ORGANISM: Artificial Sequence
<220> FEATURE:
<223> OTHER INFORMATION: HIV-1 primer

<400> SEQUENCE: 20
tccttgtctt atgtccagaa                                        20

<210> SEQ ID NO 21
<211> LENGTH: 28
<212> TYPE: DNA
<213> ORGANISM: Artificial Sequence
<220> FEATURE:
<223> OTHER INFORMATION: HIV-1 primer

<400> SEQUENCE: 21
tttggtcctt gtcttatgtc cagaatgc                               28
```

```
<210> SEQ ID NO 22
<211> LENGTH: 28
<212> TYPE: DNA
<213> ORGANISM: Artificial Sequence
<220> FEATURE:
<223> OTHER INFORMATION: HIV-1 primer

<400> SEQUENCE: 22
tactagtagt tcctgctatg tcacttcc                                          28

<210> SEQ ID NO 23
<211> LENGTH: 23
<212> TYPE: DNA
<213> ORGANISM: Artificial Sequence
<220> FEATURE:
<223> OTHER INFORMATION: HIV-1 primer

<400> SEQUENCE: 23
tgtgttatga tggtgtttaa atc                                               23

<210> SEQ ID NO 24
<211> LENGTH: 20
<212> TYPE: DNA
<213> ORGANISM: Artificial Sequence
<220> FEATURE:
<223> OTHER INFORMATION: HIV-1 primer

<400> SEQUENCE: 24
actctaaagg gttcctttgg                                                   20

<210> SEQ ID NO 25
<211> LENGTH: 26
<212> TYPE: DNA
<213> ORGANISM: Artificial Sequence
<220> FEATURE:
<223> OTHER INFORMATION: HIV-1 primer

<400> SEQUENCE: 25
tgactctggt aactagagat ccctca                                            26

<210> SEQ ID NO 26
<211> LENGTH: 30
<212> TYPE: DNA
<213> ORGANISM: Artificial Sequence
<220> FEATURE:
<223> OTHER INFORMATION: HIV-1 primer

<400> SEQUENCE: 26
tgttcaaccc tggtatctag agatccctca                                        30

<210> SEQ ID NO 27
<211> LENGTH: 20
<212> TYPE: DNA
<213> ORGANISM: Artificial Sequence
<220> FEATURE:
<223> OTHER INFORMATION: HIV-1 primer

<400> SEQUENCE: 27
ggctaactag ggacccactg                                                   20

<210> SEQ ID NO 28
<211> LENGTH: 18
<212> TYPE: DNA
<213> ORGANISM: Artificial Sequence
<220> FEATURE:
<223> OTHER INFORMATION: HIV-1 primer
```

<400> SEQUENCE: 28
actagggaac ccactgct                                                     18

<210> SEQ ID NO 29
<211> LENGTH: 26
<212> TYPE: DNA
<213> ORGANISM: Artificial Sequence
<220> FEATURE:
<223> OTHER INFORMATION: HIV-1 primer

<400> SEQUENCE: 29
tcagcaagcc gagtcctgcg tcgaga                                            26

<210> SEQ ID NO 30
<211> LENGTH: 27
<212> TYPE: DNA
<213> ORGANISM: Artificial Sequence
<220> FEATURE:
<223> OTHER INFORMATION: HIV-1 primer

<400> SEQUENCE: 30
ccgctaagcc gagccctttg cgtcgga                                           27

<210> SEQ ID NO 31
<211> LENGTH: 17
<212> TYPE: DNA
<213> ORGANISM: Artificial Sequence
<220> FEATURE:
<223> OTHER INFORMATION: HIV-1 primer

<400> SEQUENCE: 31
ggtctgaggg atctcta                                                      17

<210> SEQ ID NO 32
<211> LENGTH: 24
<212> TYPE: DNA
<213> ORGANISM: Artificial Sequence
<220> FEATURE:
<223> OTHER INFORMATION: HIV-1 primer

<400> SEQUENCE: 32
ctgctagaga ttttccacac tgac                                              24

<210> SEQ ID NO 33
<211> LENGTH: 23
<212> TYPE: DNA
<213> ORGANISM: Artificial Sequence
<220> FEATURE:
<223> OTHER INFORMATION: HIV-2 primer

<400> SEQUENCE: 33
ggctccacgc ttgcttgctt aaa                                               23

<210> SEQ ID NO 34
<211> LENGTH: 18
<212> TYPE: DNA
<213> ORGANISM: Artificial Sequence
<220> FEATURE:
<223> OTHER INFORMATION: HIV-2 primer

<400> SEQUENCE: 34
ggctccacgc ttgcttgc                                                     18

<210> SEQ ID NO 35

```
<211> LENGTH: 31
<212> TYPE: DNA
<213> ORGANISM: Artificial Sequence
<220> FEATURE:
<223> OTHER INFORMATION: HIV-2 primer

<400> SEQUENCE: 35
ttcccaaagc aagaagggtc ctaacagacc a                              31

<210> SEQ ID NO 36
<211> LENGTH: 25
<212> TYPE: DNA
<213> ORGANISM: Artificial Sequence
<220> FEATURE:
<223> OTHER INFORMATION: HBV primer

<400> SEQUENCE: 36
catgcaactt tttcacctct gccta                                     25

<210> SEQ ID NO 37
<211> LENGTH: 27
<212> TYPE: DNA
<213> ORGANISM: Artificial Sequence
<220> FEATURE:
<223> OTHER INFORMATION: HBV primer

<400> SEQUENCE: 37
aactccacag tagctccaaa ttcttta                                   27

<210> SEQ ID NO 38
<211> LENGTH: 22
<212> TYPE: DNA
<213> ORGANISM: Artificial Sequence
<220> FEATURE:
<223> OTHER INFORMATION: HCV primer

<400> SEQUENCE: 38
ccaagcttca ccatagatca ct                                        22

<210> SEQ ID NO 39
<211> LENGTH: 24
<212> TYPE: DNA
<213> ORGANISM: Artificial Sequence
<220> FEATURE:
<223> OTHER INFORMATION: HCV primer

<400> SEQUENCE: 39
ggcgacactc caccatagat cact                                      24

<210> SEQ ID NO 40
<211> LENGTH: 31
<212> TYPE: DNA
<213> ORGANISM: Artificial Sequence
<220> FEATURE:
<223> OTHER INFORMATION: HCV primer

<400> SEQUENCE: 40
ccaagcttag atcactcccc tgtgaggaac t                              31

<210> SEQ ID NO 41
<211> LENGTH: 30
<212> TYPE: DNA
<213> ORGANISM: Artificial Sequence
<220> FEATURE:
<223> OTHER INFORMATION: HCV primer

<400> SEQUENCE: 41
```

```
ccaagcttca cgcagaaagc gtctagccat                               30

<210> SEQ ID NO 42
<211> LENGTH: 24
<212> TYPE: DNA
<213> ORGANISM: Artificial Sequence
<220> FEATURE:
<223> OTHER INFORMATION: HCV primer

<400> SEQUENCE: 42
gcagaaagcg tctagccatg gcgt                                     24

<210> SEQ ID NO 43
<211> LENGTH: 26
<212> TYPE: DNA
<213> ORGANISM: Artificial Sequence
<220> FEATURE:
<223> OTHER INFORMATION: HCV primer

<400> SEQUENCE: 43
acgcagaaag cgtctagcca tggcgt                                   26

<210> SEQ ID NO 44
<211> LENGTH: 30
<212> TYPE: DNA
<213> ORGANISM: Artificial Sequence
<220> FEATURE:
<223> OTHER INFORMATION: HCV primer

<400> SEQUENCE: 44
cctccaggac cccccctccc gggagagcca                               30

<210> SEQ ID NO 45
<211> LENGTH: 27
<212> TYPE: DNA
<213> ORGANISM: Artificial Sequence
<220> FEATURE:
<223> OTHER INFORMATION: HCV primer

<400> SEQUENCE: 45
gagtacaccg gaattgccag gacgacc                                  27

<210> SEQ ID NO 46
<211> LENGTH: 21
<212> TYPE: DNA
<213> ORGANISM: Artificial Sequence
<220> FEATURE:
<223> OTHER INFORMATION: HCV primer

<400> SEQUENCE: 46
acccgctcaa tgcctggaga t                                        21

<210> SEQ ID NO 47
<211> LENGTH: 22
<212> TYPE: DNA
<213> ORGANISM: Artificial Sequence
<220> FEATURE:
<223> OTHER INFORMATION: HCV primer

<400> SEQUENCE: 47
cgaagcttgc tagccgagta gt                                       22

<210> SEQ ID NO 48
<211> LENGTH: 24
<212> TYPE: DNA
```

<213> ORGANISM: Artificial Sequence
<220> FEATURE:
<223> OTHER INFORMATION: HCV primer

<400> SEQUENCE: 48
ccgcaagact gctagccgag tagt                                    24

<210> SEQ ID NO 49
<211> LENGTH: 25
<212> TYPE: DNA
<213> ORGANISM: Artificial Sequence
<220> FEATURE:
<223> OTHER INFORMATION: HCV primer

<400> SEQUENCE: 49
gttgggtcgc gaaaggcctt gtggt                                   25

<210> SEQ ID NO 50
<211> LENGTH: 30
<212> TYPE: DNA
<213> ORGANISM: Artificial Sequence
<220> FEATURE:
<223> OTHER INFORMATION: HCV primer

<400> SEQUENCE: 50
ggtgcttgcg agtgccccgg gaggtctcgt                              30

<210> SEQ ID NO 51
<211> LENGTH: 24
<212> TYPE: DNA
<213> ORGANISM: Artificial Sequence
<220> FEATURE:
<223> OTHER INFORMATION: HCV primer

<400> SEQUENCE: 51
gacttccgag cggtcgcaac ctcg                                    24

<210> SEQ ID NO 52
<211> LENGTH: 26
<212> TYPE: DNA
<213> ORGANISM: Artificial Sequence
<220> FEATURE:
<223> OTHER INFORMATION: HCV primer

<400> SEQUENCE: 52
gcagaaagcg tctagccatg gcgtta                                  26

<210> SEQ ID NO 53
<211> LENGTH: 25
<212> TYPE: DNA
<213> ORGANISM: Artificial Sequence
<220> FEATURE:
<223> OTHER INFORMATION: HCV primer

<400> SEQUENCE: 53
gcaagcaccc tataggcagt accac                                   25

<210> SEQ ID NO 54
<211> LENGTH: 24
<212> TYPE: DNA
<213> ORGANISM: Artificial Sequence
<220> FEATURE:
<223> OTHER INFORMATION: HCV primer

<400> SEQUENCE: 54
ctcgcaagca ccctatcagg cagt                                    24

<210> SEQ ID NO 55
<211> LENGTH: 26
<212> TYPE: DNA
<213> ORGANISM: Artificial Sequence
<220> FEATURE:
<223> OTHER INFORMATION: HCV primer

<400> SEQUENCE: 55
cactcgcaag cacccctatca ggcagt                                    26

<210> SEQ ID NO 56
<211> LENGTH: 29
<212> TYPE: DNA
<213> ORGANISM: Artificial Sequence
<220> FEATURE:
<223> OTHER INFORMATION: HCV primer

<400> SEQUENCE: 56
gggaattcgc aagcacccta tcaggcagt                                  29

<210> SEQ ID NO 57
<211> LENGTH: 24
<212> TYPE: DNA
<213> ORGANISM: Artificial Sequence
<220> FEATURE:
<223> OTHER INFORMATION: HCV primer

<400> SEQUENCE: 57
ctcgcaagca ccctatcagg caga                                       24

<210> SEQ ID NO 58
<211> LENGTH: 28
<212> TYPE: DNA
<213> ORGANISM: Artificial Sequence
<220> FEATURE:
<223> OTHER INFORMATION: HCV primer

<400> SEQUENCE: 58
gcaagcaccc tatcaggcag taccacaa                                   28

<210> SEQ ID NO 59
<211> LENGTH: 27
<212> TYPE: DNA
<213> ORGANISM: Artificial Sequence
<220> FEATURE:
<223> OTHER INFORMATION: HCV primer

<400> SEQUENCE: 59
gcaagcaccc tatcaggcag taccaca                                    27

<210> SEQ ID NO 60
<211> LENGTH: 33
<212> TYPE: DNA
<213> ORGANISM: Artificial Sequence
<220> FEATURE:
<223> OTHER INFORMATION: HIV-1 probe

<400> SEQUENCE: 60
tctgcagctt cctcattgat ggtatctttt aac                             33

<210> SEQ ID NO 61
<211> LENGTH: 29
<212> TYPE: DNA
<213> ORGANISM: Artificial Sequence
<220> FEATURE:

<223> OTHER INFORMATION: HIV-1 probe

<400> SEQUENCE: 61
tcagcattat cagaaggagc cacccccaca                              29

<210> SEQ ID NO 62
<211> LENGTH: 32
<212> TYPE: DNA
<213> ORGANISM: Artificial Sequence
<220> FEATURE:
<223> OTHER INFORMATION: HIV-1 probe

<400> SEQUENCE: 62
tctgcagctt cctcattgag gtatctttta ac                           32

<210> SEQ ID NO 63
<211> LENGTH: 41
<212> TYPE: DNA
<213> ORGANISM: Artificial Sequence
<220> FEATURE:
<223> OTHER INFORMATION: HIV-1 probe

<400> SEQUENCE: 63
atcctgggat taaataaaat agtaagaatg tatagcccta c                 41

<210> SEQ ID NO 64
<211> LENGTH: 29
<212> TYPE: DNA
<213> ORGANISM: Artificial Sequence
<220> FEATURE:
<223> OTHER INFORMATION: HIV-1 probe

<400> SEQUENCE: 64
accatcaatg agggaagctg cagaatggg                               29

<210> SEQ ID NO 65
<211> LENGTH: 28
<212> TYPE: DNA
<213> ORGANISM: Artificial Sequence
<220> FEATURE:
<223> OTHER INFORMATION: HIV-1 probe

<400> SEQUENCE: 65
tctctagcag tggcgcccga acagggac                                28

<210> SEQ ID NO 66
<211> LENGTH: 34
<212> TYPE: DNA
<213> ORGANISM: Artificial Sequence
<220> FEATURE:
<223> OTHER INFORMATION: HIV-1 probe

<400> SEQUENCE: 66
accagagtca cacaacagac gggcacacac tact                         34

<210> SEQ ID NO 67
<211> LENGTH: 31
<212> TYPE: DNA
<213> ORGANISM: Artificial Sequence
<220> FEATURE:
<223> OTHER INFORMATION: HIV-2 probe

<400> SEQUENCE: 67
tcctagtcgc cgcctggtca ttcggtgttc a                            31

```
<210> SEQ ID NO 68
<211> LENGTH: 33
<212> TYPE: DNA
<213> ORGANISM: Artificial Sequence
<220> FEATURE:
<223> OTHER INFORMATION: HBV probe

<400> SEQUENCE: 68
ccaagctgtg ccttgggtgg ctttggggca tgg                              33

<210> SEQ ID NO 69
<211> LENGTH: 33
<212> TYPE: DNA
<213> ORGANISM: Artificial Sequence
<220> FEATURE:
<223> OTHER INFORMATION: HCV probe

<400> SEQUENCE: 69
gggagagcca tagtggtctg cggaaccggt gag                              33

<210> SEQ ID NO 70
<211> LENGTH: 33
<212> TYPE: DNA
<213> ORGANISM: Artificial Sequence
<220> FEATURE:
<223> OTHER INFORMATION: HCV probe

<400> SEQUENCE: 70
ccgggagagc catagtggtc tgcggaaccg gtg                              33

<210> SEQ ID NO 71
<211> LENGTH: 33
<212> TYPE: DNA
<213> ORGANISM: Artificial Sequence
<220> FEATURE:
<223> OTHER INFORMATION: HCV probe

<400> SEQUENCE: 71
caccggttcc gcagaccact atggctctcc cgg                              33

<210> SEQ ID NO 72
<211> LENGTH: 33
<212> TYPE: DNA
<213> ORGANISM: Artificial Sequence
<220> FEATURE:
<223> OTHER INFORMATION: HCV probe

<400> SEQUENCE: 72
caccggttcc gcagaccact atggctctcc cgg                              33

<210> SEQ ID NO 73
<211> LENGTH: 31
<212> TYPE: DNA
<213> ORGANISM: Artificial Sequence
<220> FEATURE:
<223> OTHER INFORMATION: HCV probe

<400> SEQUENCE: 73
cagaattcat tgccatagag gggccaagga t                                31

<210> SEQ ID NO 74
<211> LENGTH: 28
<212> TYPE: DNA
<213> ORGANISM: Artificial Sequence
<220> FEATURE:
<223> OTHER INFORMATION: HCV probe
```

```
<400> SEQUENCE: 74
tctctcgccc atctcctacc gcattggc                                    28

<210> SEQ ID NO 75
<211> LENGTH: 31
<212> TYPE: DNA
<213> ORGANISM: Artificial Sequence
<220> FEATURE:
<223> OTHER INFORMATION: HCV probe

<400> SEQUENCE: 75
cggtgtactc accgttccgc agaccactat g                                31

<210> SEQ ID NO 76
<211> LENGTH: 34
<212> TYPE: DNA
<213> ORGANISM: Artificial Sequence
<220> FEATURE:
<223> OTHER INFORMATION: HCV probe

<400> SEQUENCE: 76
tgggcgtgcc cccgcaagac tgctagccga gtag                             34
```